United States Patent
O'Connor et al.

(10) Patent No.: US 7,488,725 B2
(45) Date of Patent: Feb. 10, 2009

(54) PYRROLIDINYL BETA-AMINO AMIDE-BASED INHIBITORS OF DIPEPTIDYL PEPTIDASE IV AND METHODS

(75) Inventors: Stephen P. O'Connor, Stockton, NJ (US); Lawrence G. Hamann, North Grafton, MA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 75 days.

(21) Appl. No.: 11/589,409

(22) Filed: Oct. 30, 2006

(65) Prior Publication Data

US 2007/0099913 A1    May 3, 2007

Related U.S. Application Data

(60) Provisional application No. 60/731,795, filed on Oct. 31, 2005.

(51) Int. Cl.
*C07D 207/06* (2006.01)
*C07D 207/14* (2006.01)
*C07D 401/06* (2006.01)
*C07D 403/06* (2006.01)
*C07D 413/06* (2006.01)
*A61K 31/40* (2006.01)
*A61K 31/422* (2006.01)
*A61K 31/4709* (2006.01)
*A61K 31/538* (2006.01)
*A61K 31/55* (2006.01)
*A61P 3/00* (2006.01)

(52) U.S. Cl. .............. 514/213.01; 514/230.5; 514/312; 514/343; 514/378; 514/414; 514/423; 540/593; 544/105; 546/165; 548/247; 548/468; 548/540

(58) Field of Classification Search ............... None
See application file for complete search history.

(56) References Cited

U.S. PATENT DOCUMENTS

| | | | | |
|---|---|---|---|---|
| 6,011,155 | A | * | 1/2000 | Villhauer ............... 544/333 |
| 2008/0015146 | A1 | * | 1/2008 | Edwards et al. ......... 514/12 |
| 2008/0027035 | A1 | * | 1/2008 | Edwards et al. ...... 514/210.17 |

FOREIGN PATENT DOCUMENTS

| | | |
|---|---|---|
| EP | 1 604 989 | 12/2005 |
| EP | 1 702 916 | 9/2006 |
| WO | WO 03/000181 | 1/2003 |
| WO | WO 2004/089362 | 10/2004 |
| WO | WO 2005/056003 | 6/2005 |

OTHER PUBLICATIONS

Edmondson et al., Bioorganic & Medicinal Chemistry Letters, 14(20), 5151-5155, 2004.*
Nordhoff et al., Bioorganic & Medicinal Chemistry Letters, 16(6), 1744-1748, 2006.*
Tidwell, T., "Oxidation of Alcohols by Activated Dimethyl Sulfoxide and Related Reactions: An Update", Synthesis, pp. 857-870 (Oct. 1990).
Myers, A. et al., "Synthesis of highly epimerizable N-protected α-amino aldehydes of high enantiomeric excess", Tetrahedron Letters, vol. 41, pp. 1359-1362 (2000).
Abdel-Magid, A. et al., "Reductive Amination of Aldehydes and Ketones with Sodium Triacetoxyborohydride. Studies on Direct and Indirect Reductive Animation Procedures", Journal of Organic Chemistry, vol. 61, pp. 3849-3862 (1996).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-7734 (1997).
Rahfeld, J. et al., "Extended Investigation of the Substrate Specificity of Dipeptidyl Peptidase IV from Pig Kidney", Biol. Chem. Hoppe-Seyler, vol. 372, pp. 313-318 (May 1991).
Nagatsu, T., et al., "New Chromogenic Substrates for X-Prolyl Dipeptidyl-Aminopeptidase", Analytical Biochemistry, vol. 74, pp. 466-476 (1976).

* cited by examiner

*Primary Examiner*—Fiona T Powers
(74) *Attorney, Agent, or Firm*—Burton Rodney

(57) ABSTRACT

Compounds are provided having the formula:

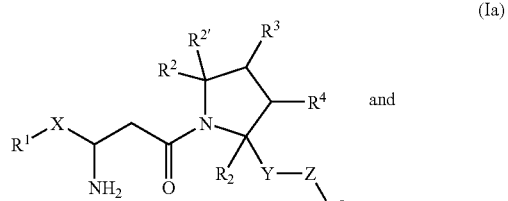

(Ia)

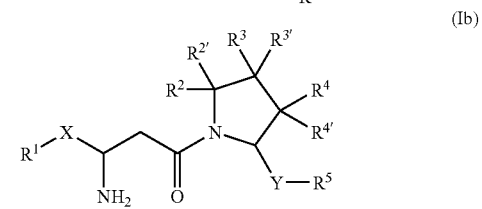

(Ib)

wherein $R^1$, $R^2$, $R^{2'}$, $R^3$, $R^{3'}$, $R^4$, $R^{4'}$, $R^5$, X, Y and Z are as defined herein.

20 Claims, No Drawings

PYRROLIDINYL BETA-AMINO AMIDE-BASED INHIBITORS OF DIPEPTIDYL PEPTIDASE IV AND METHODS

RELATED APPLICATION

This application claims priority benefit under Title 35 § 119(e) of U.S. Provisional Application No. 60/731,795, filed Oct. 31, 2005, the contents of which are herein incorporated by reference.

FIELD OF THE INVENTION

The present invention relates to beta-amino amides of substituted pyrrolidines as inhibitors of dipeptidyl peptidase IV (DPP-4), and to a method for treating multiple diseases or disorders by employing such beta-amino acid amides of substituted pyrrolidines alone, or in combination with another type of therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1 (7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo (t½≈1.5 min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1 (7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

DESCRIPTION OF THE INVENTION

In accordance with the present invention, compounds of formula (Ia) are provided

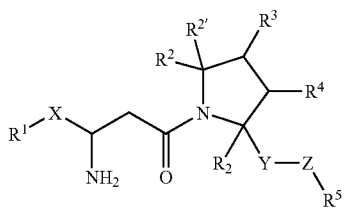

(Ia)

wherein:
$R^1$ is selected from aryl, heteroaryl or cycloheteroalkyl, wherein said aryl or heteroaryl may optionally be substituted with 1-5 substituents selected from the group consisting of halo, $C_{1-6}$ alkyl, and $C_{1-6}$ polyhaloalkyl, and said cycloheteroalkyl may optionally be substituted with 1-5 substituents selected from the group consisting of $C_{1-6}$ alkyl, halo, oxo (=O) and $C_{1-6}$ perhaloalkyl;

$R^2$ and $R^{2'}$ are each independently selected from hydrogen, $C_{1-6}$ alkyl, and $C_{1-6}$ perhaloalkyl;

$R^3$ and $R^4$ are each independently selected from hydrogen, $OR^6$ and $NR^7R^8$, wherein at least one of $R^3$ and $R^4$ is not hydrogen;

$R^5$ is selected from aryl and heteroaryl wherein said aryl and heteroaryl may optionally be substituted with 1-5 substituents selected from the group consisting of halo, $C_{1-6}$ alkyl, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkoxycarbonyl, $C_{2-6}$ alkenyl, $C_{2-6}$ alkynyl, $C_{3-6}$ cycloalkyl, $C_{3-6}$ cycloalkylalkyl, polycycloalkyl, heteroarylamino, arylamino, cycloheteroalkyl, cycloheteroalkylalkyl, hydroxy, $C_{1-6}$ hydroxyalkyl, nitro, cyano, amino, $C_{1-6}$ alkylamino, $C_{1-6}$ dialkylamino, thiol, $C_{1-6}$ alkylthio, aminocarbonyl, $C_{2-6}$ alkynylaminocarbonyl, $C_{1-6}$ alkylaminocarbonyl, $C_{2-6}$ alkenylaminocarbonyl, $C_{1-6}$ alkylcarbonyloxy, $C_{1-6}$ alkylcarbonylamino, arylcarbonylamino, heteroarylcarbonylamino, $C_{1-6}$ alkylsulfonylamino, arylsulfonylamino, heteroarylsulfonylamino, $C_{1-6}$ alkylaminocarbonylamino, $C_{1-6}$ alkoxycarbonylamino, $C_{1-6}$ alkylsulfonyl, arylsulfonyl, heteroarylsulfonyl, and sulfonamido;

$R^6$ is selected from hydrogen, $C_{1-6}$ alkyl, and $C_{3-6}$ cycloalkyl;

$R^7$ and $R^8$ are each independently selected from hydrogen, $C_{1-6}$ alkyl, $C_{3-6}$ cycloalkyl, —CO—($C_{1-6}$ alkyl), —CO-aryl, —CO-heteroaryl, —CONH$_2$, —CONH($C_{1-6}$ alkyl), CON($C_{1-6}$ alkyl)$_2$, —SO$_2$($C_{1-6}$ alkyl), —SO$_2$-aryl, and —SO$_2$-heteroaryl;

X is a methylene group or a bond, wherein the methylene group may be optionally substituted with one or two fluorine atoms;

Y is a methylene group, wherein said methylene group optionally be substituted with one or two fluorine atoms, or Y and Z together may optionally form a bond;

Z is selected from a bond, —NR$^6$—, —O—, —SO$_n$—, —N(R$^6$)SO$_2$— and —SO$_2$N(R$^6$)—, or Z and R$^5$ may be taken together to form

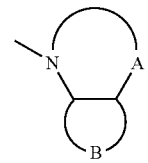

wherein A forms a 5 to 8 membered cycloheteroalkyl and B is a fused 5 to 7 member ring system selected from aryl and heteroaryl, wherein said ring system may optionally be substituted with one to five groups selected from the group consisting of halo, $C_{1-6}$ alkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkoxycarbonyl, $C_{2-6}$ alkenyl, $C_{2-6}$ alkynyl, $C_{3-6}$ cycloalkyl, $C_{3-6}$ cycloalkylalkyl, polycycloalkyl, heteroarylamino, arylamino, cycloheteroalkyl, cycloheteroalkylalkyl, hydroxy, $C_{1-6}$ hydroxyalkyl, nitro, cyano, amino, $C_{1-6}$ alkylamino, $C_{1-6}$ dialkylamino, thiol, $C_{1-6}$ alkylthio, aminocarbonyl, $C_{2-6}$ alkynylaminocarbonyl, $C_{1-6}$ alkylaminocarbonyl, $C_{2-6}$ alkenylaminocarbonyl, $C_{1-6}$ alkylcarbonyloxy, $C_{1-6}$ alkylcarbonylamino, arylcarbonylamino, heteroarylcarbonylamino, $C_{1-6}$ alkylsulfonylamino, arylsulfonylamino, heteroarylsulfonylamino, $C_{1-6}$ alkylaminocarbonylamino, $C_{1-6}$ alkoxycarbonylamino, $C_{1-6}$ alkylsulfonyl, arylsulfonyl, heteroarylsulfonyl, and sulfonamido; and n is 0-2.

In a further embodiment of the invention is provided compounds of formula Ib

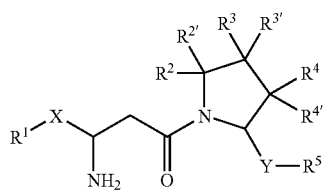

(Ib)

wherein $R^1$ is selected from aryl, heteroaryl or cycloheteroalkyl, wherein said aryl or heteroaryl may optionally be substituted with 1-5 substituents selected from the group consisting of halo, $C_{1-6}$ alkyl, and $C_{1-6}$ polyhaloalkyl, and said cycloheteroalkyl may optionally be substituted with 1-5 substituents selected from the group consisting of $C_{1-6}$ alkyl, halo, oxo (=O) and $C_{1-6}$ perhaloalkyl;

$R^2$ and $R^{2'}$ are each independently selected from hydrogen, $C_{1-6}$ alkyl, and $C_{1-6}$ perhaloalkyl;

$R^3$, $R^{3'}$, $R^4$, $R^{4'}$ are each independently selected from hydrogen, fluorine, $C_{1-6}$ alkyl, $C_{1-6}$ perhaloalkyl, $OR^6$, and $NR^7R^8$;

$R^5$ is selected from aryl and heteroaryl, wherein said aryl and heteroaryl may optionally be substituted with 1-5 substituents selected from the group consisting of halo, $C_{1-6}$ alkyl, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkoxycarbonyl, $C_{2-6}$ alkenyl, $C_{2-6}$ alkynyl, $C_{3-6}$ cycloalkyl, $C_{3-6}$ cycloalkylalkyl, polycycloalkyl, heteroarylamino, arylamino, cycloheteroalkyl, cycloheteroalkylalkyl, hydroxy, $C_{1-6}$ hydroxyalkyl, nitro, cyano, amino, $C_{1-6}$ alkylamino, $C_{1-6}$ dialkylamino, thiol, $C_{1-6}$ alkylthio, aminocarbonyl, $C_{1-6}$ alkynylaminocarbonyl, $C_{1-6}$ alkylaminocarbonyl, $C_{2-6}$ alkenylaminocarbonyl, $C_{2-6}$ alkylcarbonyloxy, $C_{1-6}$ alkylcarbonylamino, arylcarbonylamino, heteroarylcarbonylamino, $C_{1-6}$ alkylsulfonylamino, arylsulfonylamino, heteroarylsulfonylamino, $C_{1-6}$ alkylaminocarbonylamino, $C_{1-6}$ alkoxycarbonylamino, $C_{1-6}$ alkylsulfonyl, arylsulfonyl, heteroarylsulfonyl and sulfonamido, or $R^5$ is

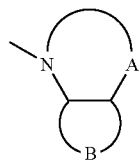

wherein A forms a 5 to 8 membered cycloheteroalkyl and B is a fused 5 to 7 member ring system selected from aryl and heteroaryl, wherein said ring system my optionally be substituted with one to five groups selected from the group consisting of halo, $C_{1-6}$ alkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkoxycarbonyl, $C_{2-6}$ alkenyl, $C_{2-6}$ alkynyl, $C_{3-6}$ cycloalkyl, $C_{3-6}$ cycloalkylalkyl, polycycloalkyl, heteroarylamino, arylamino, cycloheteroalkyl, cycloheteroalkylalkyl, hydroxy, $C_{1-6}$ hydroxyalkyl, nitro, cyano, amino, $C_{1-6}$ alkylamino, $C_{1-6}$ dialkylamino, thiol, $C_{1-6}$ alkylthio, aminocarbonyl, $C_{2-6}$ alkynylaminocarbonyl, $C_{1-6}$ alkylaminocarbonyl, $C_{2-6}$ alkenylaminocarbonyl, $C_{1-6}$ alkylcarbonyloxy, $C_{1-6}$ alkylcarbonylamino, arylcarbonylamino, heteroarylcarbonylamino, $C_{1-6}$ alkylsulfonylamino, arylsulfonylamino, heteroarylsulfonylamino, $C_{1-6}$ alkylaminocarbonylamino, $C_{1-6}$ alkoxycarbonylamino, $C_{1-6}$ alkylsulfonyl, arylsulfonyl, heteroarylsulfonyl and sulfonamido;

$R^6$ is selected from hydrogen, $C_{1-6}$ alkyl and $C_{3-6}$ cycloalkyl;

$R^7$ and $R^8$ are each independently selected from hydrogen, $C_{1-6}$ alkyl, $C_{3-6}$ cycloalkyl, —CO—($C_{1-6}$ alkyl), —CO-aryl, —CO-heteroaryl, —CONH$_2$, —CONH($C_{1-6}$ alkyl), CON($C_{1-6}$ alkyl)$_2$, —SO$_2$($C_{1-6}$ alkyl), —SO$_2$-aryl and —SO$_2$-heteroaryl;

X is a methylene group or a bond, wherein the methylene group may be optionally substituted with one or two fluorine atoms;

Y is a methylene group, wherein said methylene group optionally be substituted with one or two fluorine atoms, or a bond; and n is 0-2.

The definition of formula Ia and Ib above include all pharmaceutically acceptable salts, stereoisomers, and prodrug esters of formula Ia and Ib.

The compounds of formula I possess activity as inhibitors of DPP-4 in vivo and are useful in the treatment of diabetes and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, such as retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

In the above method of the invention, the compound of formula (I) will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

DETAILED DESCRIPTION OF THE INVENTION

Compounds of formula Ia may be generated by the methods shown in Schemes 1-5 and the descriptions thereof.

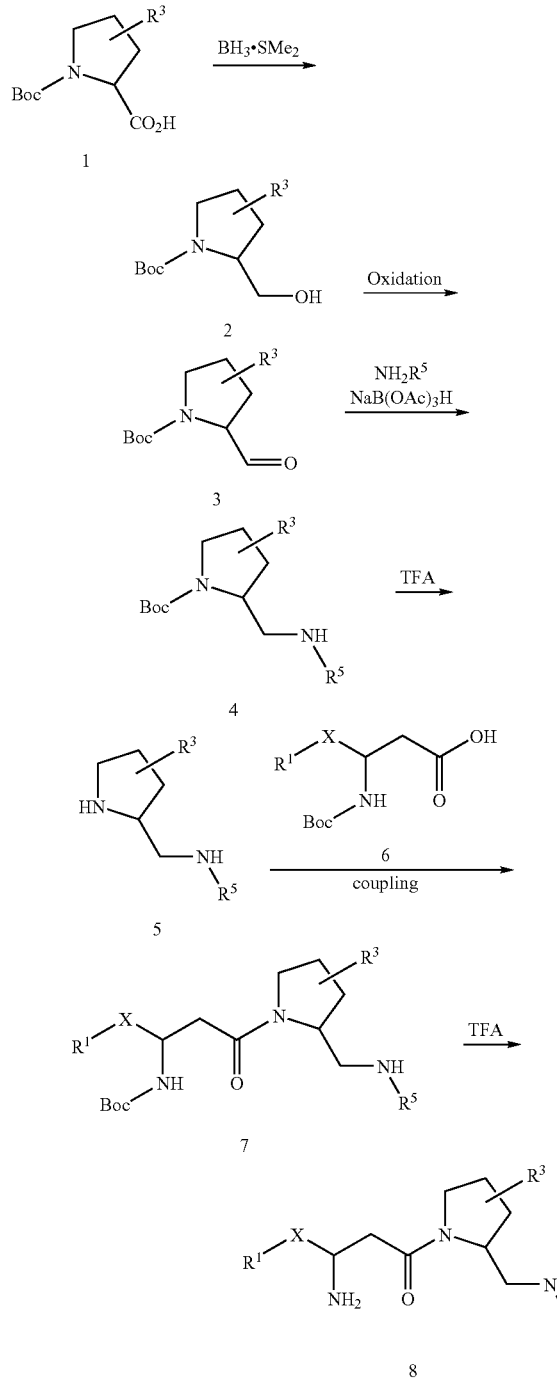

Scheme 1 provides a general route to compounds of formula Ia. Compounds 1 in which $R^3$ at C-3 or C-4 of the pyrrolidine ring is NHFMOC, of which both isomers are commercially available in the natural 2-(S)-series, may be elaborated through FMOC removal and subsequent alkylation, acylation, or sulfonylation by methods known to those skilled in the art to provide addition analogs. In a similar manner compounds with $R^3$ being OH or OP (P=protecting group such as TBS or benzyl) at C-3 or C-4 of the pyrrolidine ring may be converted to other O-alkylated analogs with appropriate alkylating agents such as alkyl bromides or iodides and a suitable base, for example potassium carbonate or diisopropylethylamine. Reduction of the carboxylic acid may be accomplished with borane-dimethylsulfide complex to provide alcohols such as 2. The compounds 2 may be oxidized to the aldehydes using oxidation reagents such as the Dess-Martin periodinane or TPAP/NMO, or through the use of Swern conditions or other variants as described by Tidwell in *Synthesis* 1980, 1980, 857. In addition, the method of Myers et. al. (*Tetrahedron Lett.* 2000, 41, 1359) may be used for chiral, non-racemic aldehydes. Aldehydes such as 3 may converted to amines 4 under standard reductive amination conditions as described by Abdel-Magid et. al. in *J. Org. Chem.* 1996, 61, 3849, specifically by combining the aldehyde and the amine and sodium triacetoxyborohydride. Deprotection with TFA gives the diamines 5 which can be coupled with the N-Boc protected beta-amino acid compound 4 using any number of amide coupling reagents, for example EDCI to produce the protected amino amides 7. Coupling will occur preferentially at the more nucleophilic ring nitrogen relative to the less reactive $R^5$-substituted amine where $R^5$ is aryl or heteroaryl. The chiral, non-racemic N-Boc beta-amino acids 6 may be obtained commercially where available or synthesized by methods such as those described by Juaristi in *Enantioselective Synthesis of beta-Amino Acids* (Wiley-VCH, New York, 1990). Boc removal with TFA provides the amino amides 8. In addition, compounds such as 7 in which $R^3$ is a protected oxygen or nitrogen substituent may be deprotected and functionalized prior to further elaboration to compounds such as 8 by methods known to those skilled in the art.

SCHEME 2

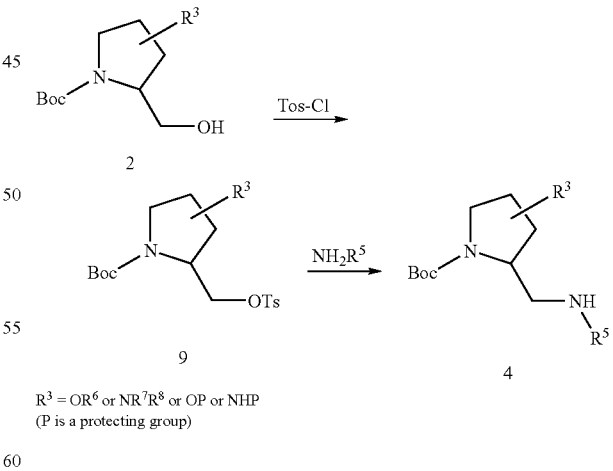

$R^3$ = $OR^6$ or $NR^7R^8$ or OP or NHP
(P is a protecting group)

Scheme 2 provides an alternative method to make amine compounds 4. The alcohols 2 may be O-tosylated using tosyl chloride in methylene chloride in the presence of TEA or in pyridine. The displacement of the tosyl group by the appropriate amine on heating in a suitable solvent such as THF, toluene, or chloroform will give compounds such as 4 which can be carried on as described in Scheme 1.

SCHEME 3

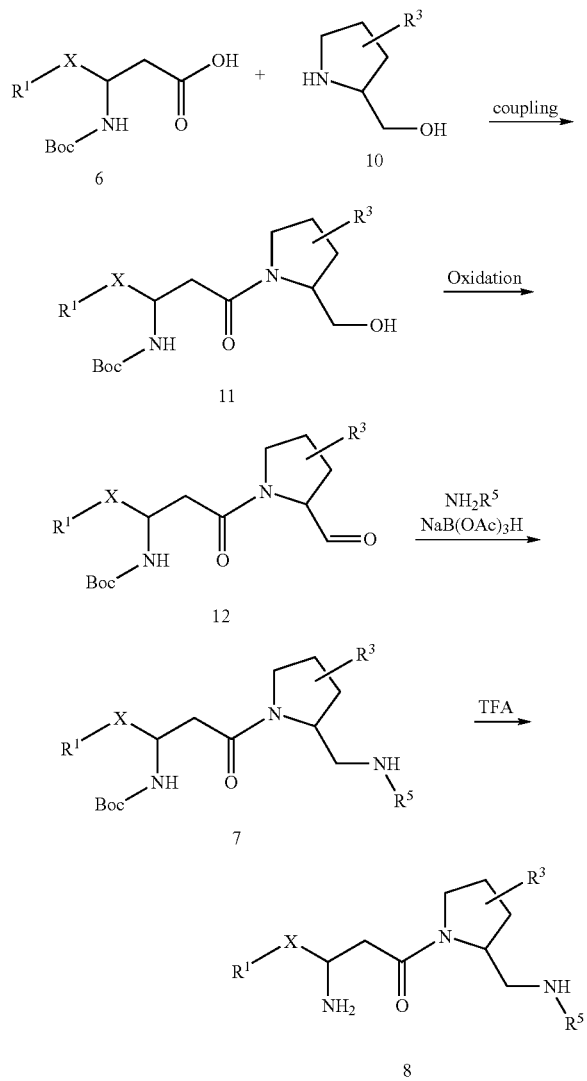

R³ = OR⁶ or NR⁷R⁸ or OP or NHP
(P is a protecting group)

SCHEME 4

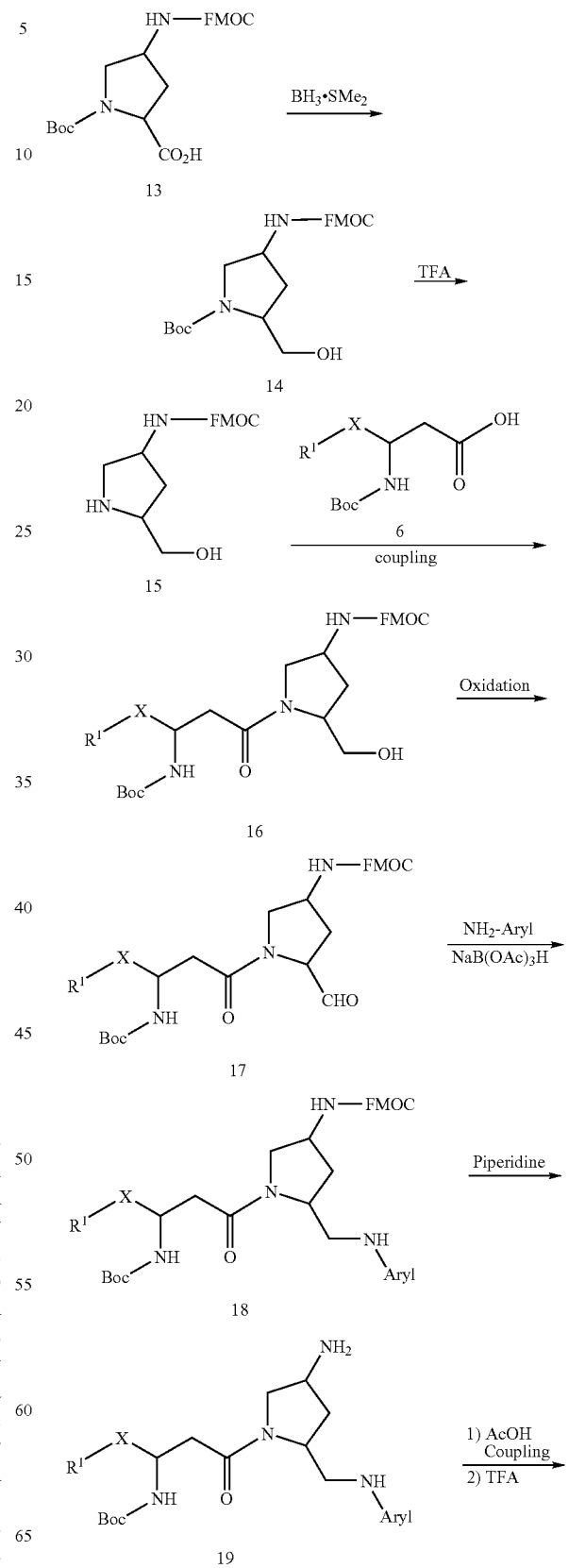

Scheme 3 provides an additional method to access compounds of structure Ia. Compounds 10 may be obtained from compounds 2 by Boc removal with TFA. Coupling of 10 with the N-Boc protected beta-amino acid compound 6 using any number of amide coupling reagents, for example EDCI, will produce the protected amino amides 11. Transformation to the aldehyde can be performed using oxidation reagents such as the Dess-Martin periodinane or TPAP/NMO, as well as under Swern conditions or other variants as described by Tidwell in *Synthesis* 1980, 1980, 857. In addition, the method of Myers et. al. (*Tetrahedron Lett.* 2000, 41, 1359) is useful for chiral, non-racemic aldehydes. Aldehydes such as 12 may converted to amines 7 under standard reductive amination conditions as described by Abdel-Magid et. al. in *J. Org. Chem.* 1996, 61, 3849, specifically by combining the aldehyde in acetonitrile with the amine and sodium triacetoxyborohydride. Deprotection with TFA gives the diamines 8.

-continued

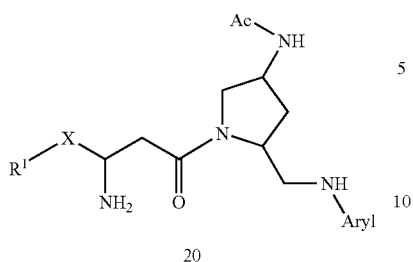
20

-continued

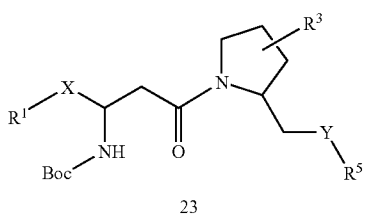
23

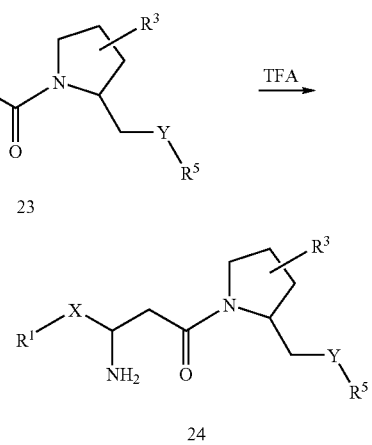
24

$R^3 = OR^6$ or $NR^7R^8$ or OP or NHP
(P is a protecting group)

In Scheme 4 are shown details which allow for the synthesis of derivatives where $R^3$ is an acylated amino substituent. Compound 13 may be reduced to the alcohol using borane-dimethylsulfide complex to give 14. Boc removal with TFA gives 15 which may be coupled with 6 using EDCI to give the alcohol 16. Transformation to the aldehydes 17 can be performed using oxidation reagents such as the Dess-Martin periodinane or TPAP/NMO, as well as under Swern conditions or other variants as described by Tidwell in *Synthesis* 1980, 1980, 857. In addition, the method of Myers et. al. (*Tetrahedron Lett.* 2000, 41, 1359) is useful for chiral, non-racemic aldehydes. Aldehydes such as 17 may converted to amines 18 using aryl- or heteroarylamines under standard reductive amination conditions as described by Abdel-Magid et. al. in *J. Org. Chem.* 1996, 61, 3849, specifically by combining the aldehyde in acetonitrile with the amine and sodium triacetoxyborohydride. Deprotection with TFA gives the amines 18. FMOC removal with piperidine to give 19 followed by acylation with a carboxlic acid, as shown for acetic acid, and subsequent Boc removal with TFA gives products 20. Similar methods known to those skilled in the art may be used to make other such 3- and 4-functionalized amino- and oxy-substituted pyrrolidine analogs.

Scheme 5 provides a method to make certain oxygen and sulfur analogs of compounds Ia. The O-tosyl derivative 9 may be reacted with an appropriate alcohol or thiol to yield compounds such as 21. For less nucleophilic components, the use of a suitable base such as sodium hydride, potassium carbonate, or lithium hexamethyldisilazide, may be necessary. Boc removal with TFA followed by coupling of 22 with 6 using EDCI would yield compounds such as 23. Boc removal with TFA yields oxy and thio analogs 24. Alternatively, compounds such as 23 where Y=S may be oxidized with reagents such as MCBA, bleach, or other oxidants known to those skilled in the art. Subsequent Boc removal with TFA yields the corresponding sulfoxide and sulfone analogs (Y=SO and $SO_2$, respectively) of 24.

Compounds of formula Ib may be generated by the methods shown in Schemes 6 to 9 and the descriptions thereof.

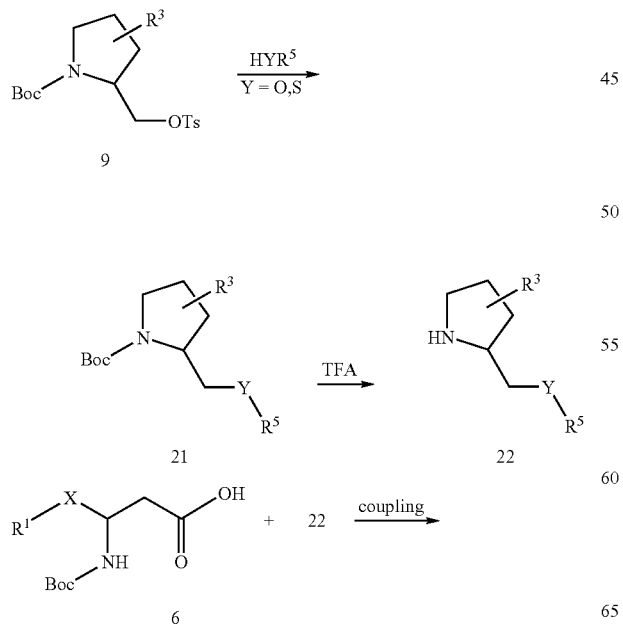

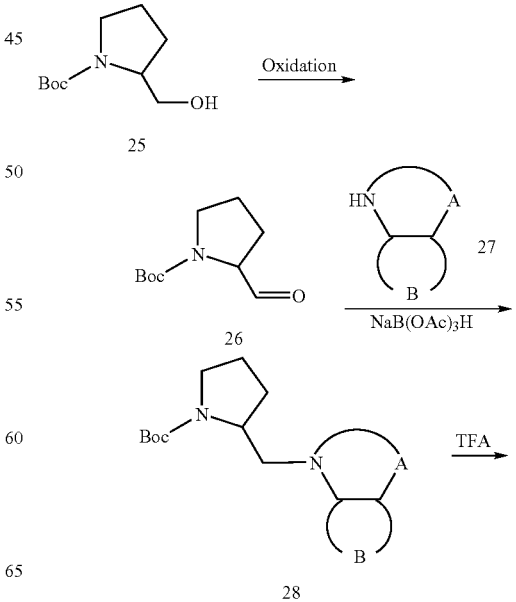

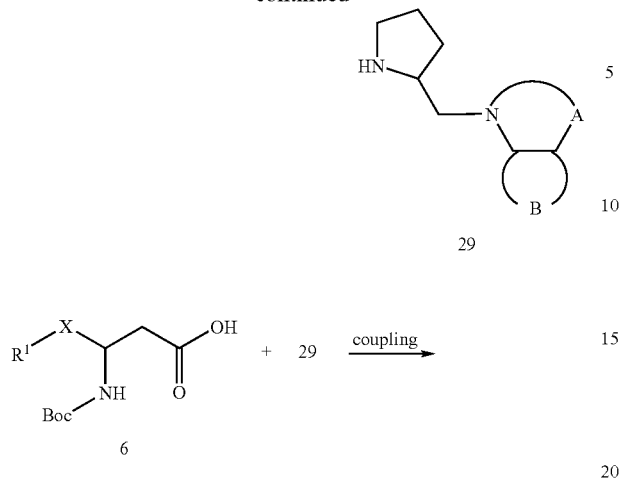

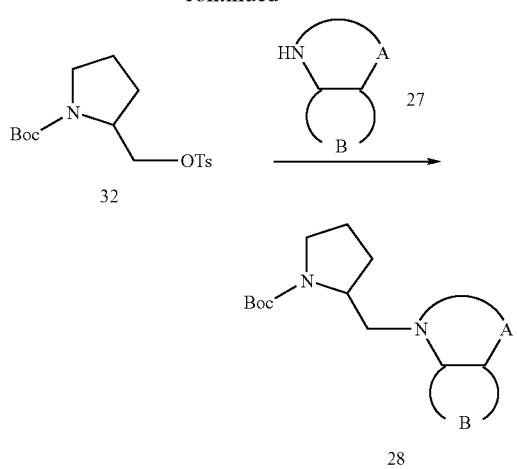

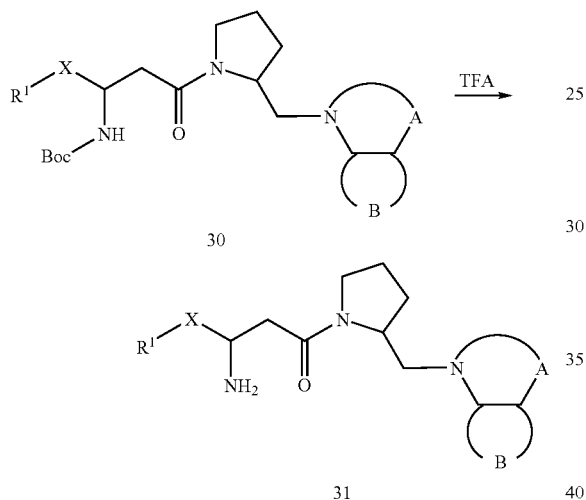

Scheme 7 provides an alternative route to intermediates described in Scheme 6. Tosylation of 25 using tosyl chloride in methylene chloride in the presence of TEA or in pyridine would give 32. The displacement of the tosyl group by the appropriate bicyclic aryl- or heteroarylamine 27 on heating in a suitable solvent such as THF, toluene, or chloroform will give compounds such as 28 which can be carried forward as described in Scheme 6.

The commercial N-Boc prolinol of Scheme 6 may be converted to the aldehyde 26 using oxidation reagents such as the Dess-Martin periodinane or TPAP/NMO, as well as under Swern conditions or other variants as described by Tidwell in *Synthesis* 1980, 1980, 857. In addition, the method of Myers et. al. (*Tetrahedron Lett.* 2000, 41, 1359) is useful for chiral, non-racemic aldehydes. Aldehyde 26 may converted to amines 28 using bicyclic aryl- or heteroarylamines under standard reductive amination conditions as described by Abdel-Magid et. al. in *J. Org. Chem.* 1996, 61, 3849, specifically by combining the aldehyde in acetonitrile with the amine and sodium triacetoxyborohydride. Deprotection with TFA gives the amines 29. Coupling of 29 with 6 using EDCI followed by Boc removal will provide compounds such as 31.

SCHEME 7

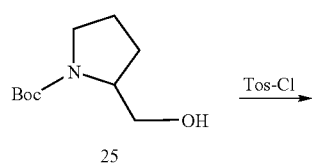

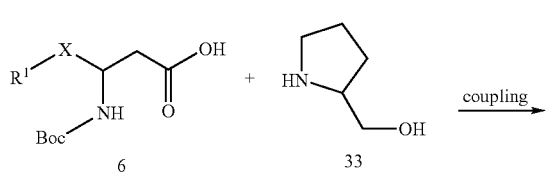

SCHEME 8

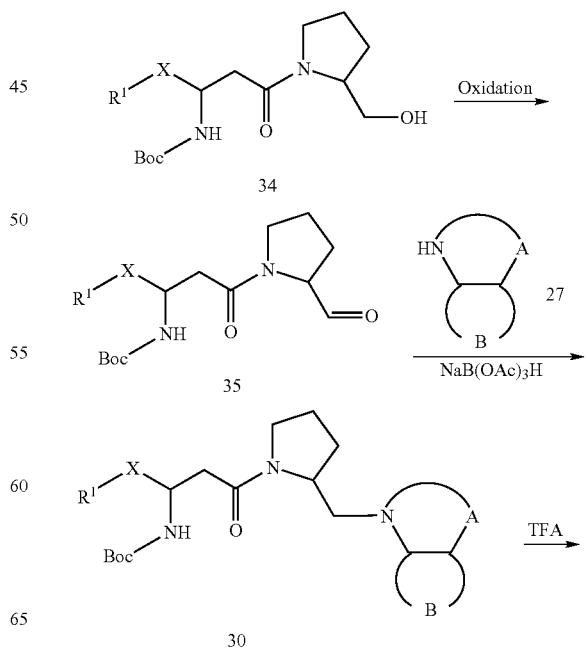

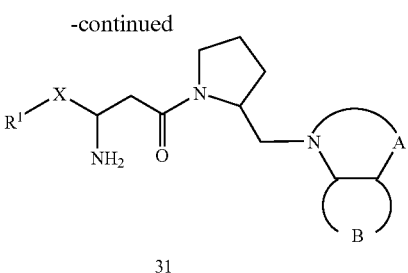

31

Scheme 8 provides an additional method to access compounds of structure Ib. Coupling of 33 with the N-Boc protected beta-amino acid compound 6 using EDCI will produce the protected amino amides 34. Transformation to the aldehyde can be performed using oxidation reagents such as the Dess-Martin periodinane or TPAP/NMO, as well as under Swern conditions or other variants as described by Tidwell in *Synthesis* 1980, 1980, 857. In addition, the method of Myers et al. (*Tetrahedron Lett.* 2000, 41, 1359) is useful for chiral, non-racemic aldehydes. Aldehydes such as 35 may converted to amines 30 using the appropriate bicyclic aryl- or heteroarylamine 27 under standard reductive amination conditions as described by Abdel-Magid et. al. in *J. Org. Chem.* 1996, 61, 3849, specifically by combining the aldehyde in acetonitrile with the amine and sodium triacetoxyborohydride. Deprotection with TFA gives the diamines 31.

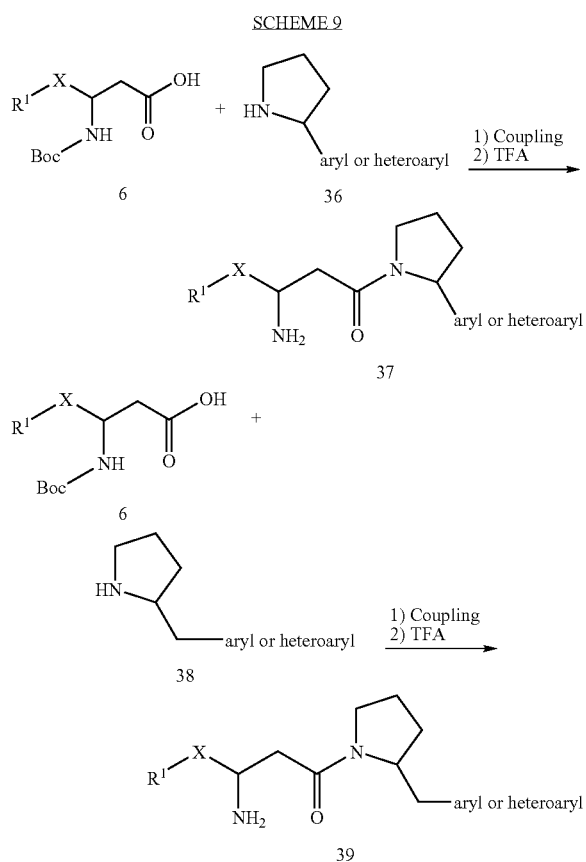

Scheme 9 provides a generalized route to aryl or heteroaryl analogs 37 and 39, respectively. Coupling 6 and either 36 or 38 using EDCI followed by Boc removal with TFA can be used to produce these compounds.

Single enantiomers of compounds produced as racemates may be resolved using chromatographic methods with columns such as the carbohydrate-based Chiralcel columns produced by Daicel. Alternatively, resolution of single enantiomers may be accomplished by the method of classical resolution using enantiomerically pure carboxylic acids followed by pH adjustment and extraction to produce the pure free base.

DEFINITIONS

The following definitions apply to the terms as used throughout this specification, unless otherwise limited in specific instances.

Unless otherwise indicated, the term "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof. Optionally, said alkyl groups may be substituted with one or more substituents, such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one or more substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Optionally, said alkynyl group may be substituted with one or more substituents, such as those substituents disclosed for alkyl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

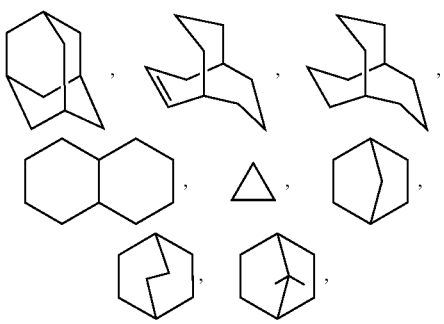

any of which groups may be optionally substituted with one or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

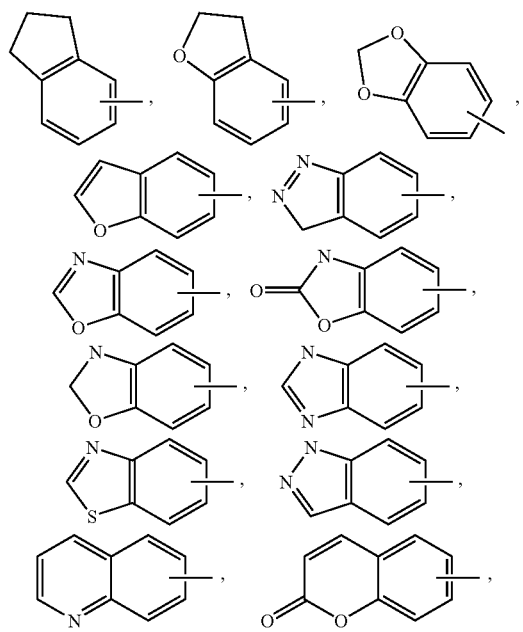

and may be optionally substituted through available carbon atoms with one or more groups selected from hydrogen, halo, haloalkyl, alkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl and/or any of the alkyl substituents set out herein.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as:

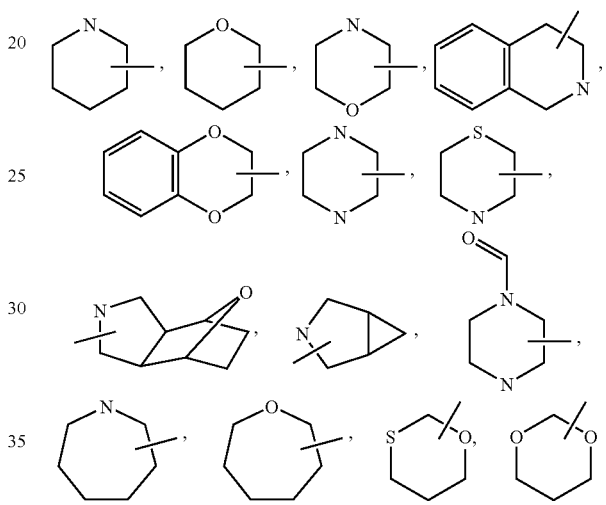

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include one or more substituents such as any of the substituents set out above for alkyl. Examples of heteroaryl groups include the following:

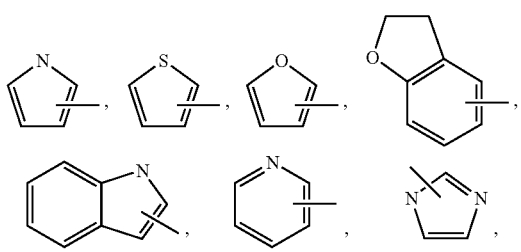

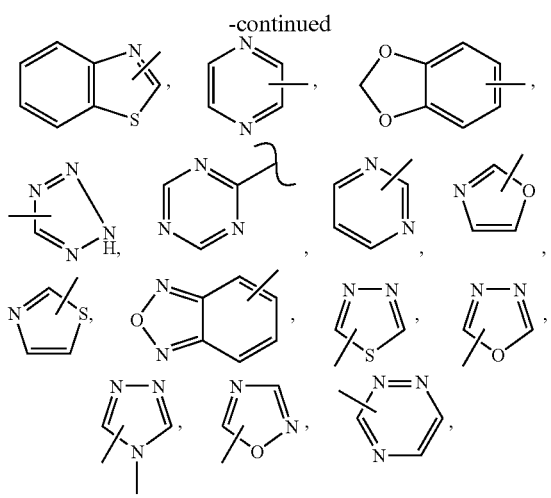

and the like.

The term "polyhaloalkyl" as used herein alone or as part of another group refers to an "alkyl" group as defined above, having 2 to 9, preferably from 2 to 5, halo substituents, such as $CF_3CH_2$, $CF_3$ or $CF_3CF_2CH_2$.

The term "polyhaloalkoxy" as used herein refers to an "alkoxy" or "alkyloxy" group as defined above having 2 to 9, preferably from 2 to 5, halo substituents, such as $CF_3CH_2O$—, $CF_3O$— or $CF_3CF_2CH_2O$—.

The term "sulfonamido" refers to —$S(O)_2$—$NR_a R_b$, wherein Ra and Rb are as defined above for "substituted amino".

The term "alkylcarbonyloxy" as used herein, refers to an "alkyl-CO—O—" group, wherein alkyl is as defined above.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etC) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The term "methylene," as used herein, refers to a —$CH_2$— group.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

The conditions, diseases and maladies collectively referred to as "diabetic complications" include retinopathy, neuropathy and nephropathy, erectile dysfunction, and other known complications of diabetes.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

UTILITIES AND COMBINATIONS

A. Utilities

The compounds of the present invention possess activity as inhibitors of dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referred to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

It is believed that the use of the compounds of formula I in combination with at least one or more other antidiabetic agent(s) provides antihyperglycemic results greater than that possible from each of these medicaments alone and greater than the combined additive anti-hyperglycemic effects produced by these medicaments. Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents and appetite suppressants.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, SGLT2 inhibitors and other dipeptidyl peptidase IV (DPP4) inhibitors.

It is believed that the use of the compound of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Wellcome's GL-262570, englitazone ($C_{1-68722}$, Pfizer) or darglitazone (C-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-HO39242 (Astra/Zeneca), GW-409544 (Glaxo-Wellcome), GW-501516 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable other DPP4 inhibitors include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899641, WO 01/68603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1,) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (CETP) inhibitors, such as C-529414 (Pfizer) and JTT-705 (Akros Pharma)), PPAR agonists (as described above) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. SoC, 1976, 98, 1291-1293, phosphinylphosphonates reported by McClard, R. W. et al, J.A.CS., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with the compound of formula I include those disclosed in Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, CardiovasC Drug Rev. (1998), 16(1), 16-30; "RP 73163: a bioavailable alkylsulfinyl-diphenylimidazole ACAT inhibitor", Smith, C, et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-$_{1-62}$, or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitors for use in combination with the compound of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR[1] antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonsist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or C331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopoamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF), WO99/00353 (KaroBio) and WO00/039077 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physician's Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred.

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The compound of formula I will be employed in a weight ratio to the meglitinide, PPAR-gamma agonist, PPAR-alpha/gamma dual agonist, aP2 inhibitor or other DPP4 inhibitor within the range from about 0.01:1 to about 100:1, preferably from about 0.2:1 to about 10:1.

The compound of formula I of the invention will be generally employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etC by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from one to four times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitory activity of the compounds of the present invention may be determined by use of an in vitro assay system which measures the degree in inhibition of DPP-4-mediated cleavage of an appropriate substrate or pseudo-substrate. Inhibition constants (Ki values) for the DPP-4 inhibitors of the invention may be determined by the method described in the experimental section below.

Purification of Porcine Dipeptidyl Peptidase IV

Porcine enzyme was purified as previously described (1), with several modifications. Kidneys from 15-20 animals were obtained, and the cortex was dissected away and frozen at −80° C. Frozen tissue (2000-2500 g) was homogenized in 12 L of 0.25 M sucrose in a Waring blender. The homogenate then was left at 37° C. for 18 hours to facilitate cleavage of DPP-4 from cell membranes. After the cleavage step, the homogenate was clarified by centrifugation at 7000×g for 20 min at 4° C., and the supernatant was collected. Solid ammonium sulfate was added to 60% saturation, and the precipitate was collected by centrifugation at 10,000×g and was discarded. Additional ammonium sulfate was added to the supernatant to 80% saturation, and the 80% pellet was collected and dissolved in 20 mM $Na_2HPO_4$, pH 7.4.

After dialysis against 20 mM $Na_2HPO_4$, pH 7.4, the preparation was clarified by centrifugation at 10,000×g. The clarified preparation then was applied to 300 mL of ConA Sepharose that had been equilibrated in the same buffer. After washing with buffer to a constant $A_{280}$, the column was eluted with 5% (w/v) methyl α-D-mannopyranoside. Active fractions were pooled, concentrated, and dialyzed against 5 mM sodium acetate, pH 5.0. Dialyzed material then was passed through a 100 mL Pharmacia Resource S column equilibrated in the same buffer. The flow through material was collected and contained most of the enzyme activity. Active material again was concentrated and dialyzed into 20 mM $Na_2HPO_4$, pH 7.4. Lastly, the concentrated enzyme was chromatographed on a Pharmacia S-200 gel filtration column to removed low molecular weight contaminants. Purity of column fractions was analyzed by reducing SDS-PAGE, and the purest fractions were pooled and concentrated. Purified enzyme was stored in 20% glycerol at −80° C.

Assay of Porcine Dipeptidyl Peptidase IV

Enzyme was assayed under steady-state conditions as previously described (2) with gly-pro-p-nitroanilide as substrate, with the following modifications. Reactions contained, in a final volume of 100 μl, 100 mM Aces, 52 mM TRIS, 52 mM ethanolamine, 500 μM gly-pro-p-nitroanilide, 0.2% DMSO, and 4.5 nM enzyme at 25° C., pH 7.4. For single assays at 10 μM test compound, buffer, compound, and enzyme were added to wells of a 96 well microtiter plate, and were incubated at rt for 5 min. Reactions were started by addition of substrate. The continuous production of p-nitroaniline was measured at 405 nM for 15 min using a Molecular Devices Tmax plate reader, with a read every 9 seconds. The linear rate of p-nitroaniline production was obtained over the linear portion of each progress curve. A standard curve for p-nitroaniline absorbance was obtained at the beginning of each experiment, and enzyme catalyzed p-nitroaniline production was quantitated from the standard curve. Compounds giving greater than 50% inhibition were selected for further analysis.

For analysis of positive compounds, steady-state kinetic inhibition constants were determined as a function of both substrate and inhibitor concentration. Substrate saturation curves were obtained at gly-pro-p-nitroanilide concentrations from 60 μM to 3600 μM. Additional saturation curves also were obtained in the presence of inhibitor. Complete inhibition experiments contained 11 substrate and 7 inhibitor concentrations, with triplicate determinations across plates. For tight binding inhibitors with $K_i$s less than 20 nM, the enzyme concentration was reduced to 0.5 nM and reaction times were increased to 120 min. Pooled datasets from the three plates were fitted to the appropriate equation for either competitive, noncompetitive or uncompetitive inhibition.

(1) Rahfeld, J. Schutkowski, M., Faust, J., Neubert, Barth, A., and Heins, J. (1991) Biol. Chem. Hoppe-Seyler, 372, 313-318.

(2) Nagatsu, T., Hino, M., Fuyamada, H., Hayakawa, T., Sakakibara, S., Nakagawa, Y., and Takemoto, T. (1976) Anal. Biochem., 74, 466-476.

ABBREVIATIONS

The following abbreviations are employed in the Examples and elsewhere herein:
Ph=phenyl
Bn=benzyl
i-Bu=iso-butyl
Me=methyl
Et=ethyl
Pr=propyl
Bu=butyl
TMS=trimethylsilyl
FMOC=fluorenylmethoxycarbonyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
DMSO=dimethylsulfoxide
EtOAc=ethyl acetate
THF=tetrahydrofuran
TFA=trifluoroacetic acid
$Et_2NH$=diethylamine
MCBA=meta-chloroperoxybenzoic acid
NMM=N-methylmorpholine
NMO=N-methylmorpholine N-oxide
n-BuLi=n-butyllithium
Pd/C=palladium on carbon
$PtO_2$=platinum oxide
TBSCl=tert-butyldimethylsilyl chloride
TEA=triethylamine
TPAP=tetrapropylammonium perruthenate
min=minute(s)
h or hr=hour(s)
L=liter
mL=milliliter
μL=microliter
g=gram(s)
mg=milligram(s)
mol=mole(s)
mmol=millimole(s)

meq=milliequivalent
rt=room temperature
sat or sat'd=saturated
aq.=aqueous
TLC=thin layer chromatography
$t_R$=retention time
mp=melting point
HPLC=high performance liquid chromatography
LC/MS=high performance liquid chromatography/mass spectrometry
MS or Mass Spec=mass spectrometry
NMR=nuclear magnetic resonance
EDCI or EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT·$H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
equiv=equivalent(s)
UCT=United Chemical Technologies, InC; Bristol, Pa.

EXAMPLES

The following examples are provided to describe the invention in further detail. These examples, which set forth the best mode presently contemplated for carrying out the invention, are intended to illustrate and not to limit the invention.

General

The following analytical and purification methods were used in the synthesis of the compounds described.

LC Method 1: Phenomenex Luna, 5 u, 4.6×50 mm column; detection at 220 nm; flow rate 4 mL/min; 4 min linear gradient from 10:90 methanol:water (containing 0.1% TFA) to 90:10 methanol:water (containing 0.1% TFA).

LC Method 2: YMC S5 ODS Combiscreen 4.6×50 mm column; detection at 220 nm; flow rate 4 mL/min; 4 min linear gradient from 10:90 methanol:water (containing 0.2% phosphoric acid) to 90:10 methanol:water (containing 0.2% phosphoric acid).

LC Method 3: Phenomenex Luna, 5 u, 4.6×50 mm column; detection at 220 nm; flow rate 4 mL/min; 4 min linear gradient from 10:90 methanol:water (containing 0.2% phosphoric acid) to 90:10 methanol:water (containing 0.2% phosphoric acid).

LCMS Method 1: Phenomenex Luna, 5 u, 4.6×50 mm; detection at 220 nm; flow rate 4 mL/min; 4 min linear gradient from 10:90 methanol:water (containing 0.1% TFA) to 90:10 methanol:water (containing 0.1% TFA). LRMS (ESI, pos. ion spectrum): m/z reported for M+H ion.

Cartridge Method 1: A UCT C-18 cartridge [part #CEC181 (2500)6] was prewashed with acetonitrile (20 ml) and water (20 ml). The reaction mixture was then loaded onto the cartridge. The cartridge was washed with water then a step gradient of 20% to 80% acetonitrile in water.

Prep LC Method 1: Phenomenex Luna 5 u 21.2×100 mm column; detection at 220 nm; flow rate 20 mL/min; 10 min linear gradient from 90:10 water:methanol (containing 0.1% TFA) to 10:90 water:methanol (containing 0.1% TFA).

Prep LC Method 2: YMC S5 ODS 30×100 mm column; detection at 220 nm; flow rate 20 mL/min; 10 min linear gradient from 90:10 water:methanol (containing 0.1% TFA) to 10:90 water:methanol (containing 0.1% TFA).

Example 1

Step A:

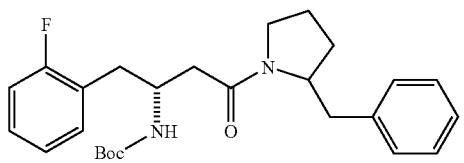

To a solution of (3R)-3-(Boc-amino)-4-(2-fluorophenyl) butanoic acid (60 mg, 0.2 mmol) in 0.6 mL acetonitrile were added HOAT (41 mg, 0.30 mmol) and EDCI (77 mg, 0.40 mmol). After 5 minutes 2-benzylpyrrolidine (33 mg, 0.20 mmol) was added. After an additional 20 minutes, EtOAc (2 mL) was added and the mixture washed sequentially with 2×2 mL of saturated aq. sodium bicarbonate, 2×2 mL saturated aq. ammonium chloride, 2 mL of water. The organic layer was then dried with magnesium and concentrated to yield product (76 mg, 0.17 mmol, 86%) as an amber oil. Analysis by LC (LC Method 1; $t_R$=3.9 min) and LC-MS (LCMS Method 1; M+H=441, $t_R$=3.9 min) indicated 96% pure product.

Step B:

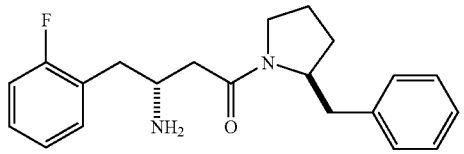

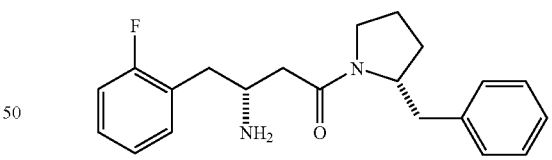

To the product from step A (76 mg, 0.17 mmol) in methylene chloride (1 mL) was added TFA (1 mL). After 48 minutes the solvent was removed in vacuo, the residue passed thru a UCT C-18 cartridge [part #CEC181(2500)6] with water then methanol to elute product. Concentration of product containing fractions followed by preparative chiral LC on a Daicel OJ column eluting with 20% isopropanol in heptane provided 21 mg (0.046 mmol) of Isomer A and 9 mg (0.020 mmol) of Isomer B as tan foams. Analysis of Isomer A by LC (LC Method 1; $t_R$=2.4 min) and LC-MS (LCMS Method 1; M+H=341, $t_R$=2.9 min) indicated 100% pure product. Analysis of Isomer B by LC (LC Method 1; $t_R$=2.5 min) and LC-MS (LCMS Method 1; M+H=341, $t_R$=2.9 min) indicated 100% pure product.

Example 2

Step A:

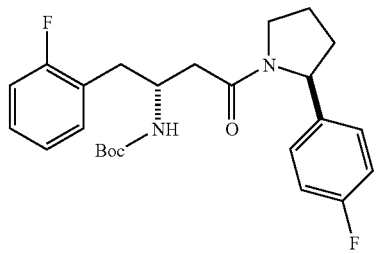

To a solution of (3R)-3-(Boc-amino)-4-(2-fluorophenyl)butanoic acid (60 mg, 0.2 mmol) in 0.6 mL acetonitrile were added HOAT (41 mg, 0.30 mmol) and EDCI (77 mg, 0.40 mmol). After 5 minutes (S)-2-(4-fluorophenyl)pyrrolidine (33 mg, 0.20 mmol) was added. After an additional 13 minutes, EtOAc (2 mL) was added and the mixture washed sequentially with 2×2 mL of saturated aq. sodium bicarbonate, 2×2 mL saturated aq. ammonium chloride, 2 mL of water. The organic layer was then dried with magnesium and concentrated to yield product (73 mg, 0.16 mmol, 82%) as an off-white foam. Analysis by LC (LC Method 1; $t_R$=3.8 min) and LC-MS (LCMS Method 1; M+H=445, $t_R$=3.7 min) indicated 100% pure product.

Step B:

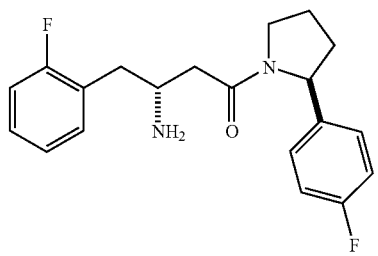

To the product from step A (73 mg, 0.16 mmol) in methylene chloride (1 mL) was added TFA (1 mL). After 24 minutes the solvent was removed in vacuo, the residue passed thru a UCT C-18 cartridge [part #CEC181(2500)6] with water then 50% methanol/water to elute product. Concentration of product containing fractions provided 62 mg (0.14 mmol, 83%) of product as a white foam. Analysis by LC (LC Method 1; $t_R$=2.2 min) and LC-MS (LCMS Method 1; M+H=345, $t_R$=2.6 min) indicated 100% pure product.

Example 3

Step A:

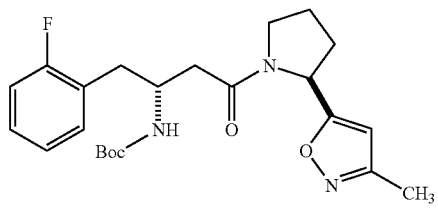

To a solution of (3R)-3-(Boc-amino)-4-(2-fluorophenyl)butanoic acid (48 mg, 0.16 mmol) in 0.6 mL acetonitrile were added HOAT (33 mg, 0.24 mmol) and EDCI (62 mg, 0.32 mmol). After 5 minutes (S)-2-(3-methylisoxazol-5-yl)pyrrolidine (25 mg, 0.16 mmol) was added. After an additional 30 minutes, EtOAc (2 mL) was added and the mixture washed sequentially with 2×2 mL of saturated aq. sodium bicarbonate, 2×2 mL saturated aq. ammonium chloride, 2 mL of water. The organic layer was then dried with magnesium and concentrated to yield product (47 mg, 0.11 mmol, 68%) as a white foam. Analysis by LC (LC Method 1; $t_R$=3.3 min) and LC-MS (LCMS Method 1; M+H=432, $t_R$=3.3 min) indicated 99% pure product.

Step B:

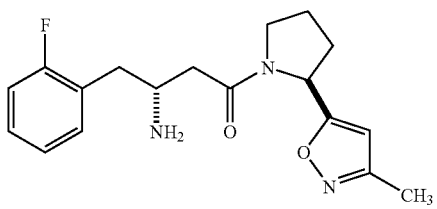

To the product from step A (47 mg, 0.11 mmol) in methylene chloride (1 mL) was added TFA (1 mL). After 25 minutes the solvent was removed in vacuo, the residue passed thru a UCT C-18 cartridge [part #CEC181(2500)6] with water then 50% methanol/water to elute product. Concentration of product containing fractions provided 49 mg (0.11 mmol, 100%) of product as a clear, colorless oil. Analysis by LC (LC Method 1; $t_R$=1.6 min) and LC-MS (LCMS Method 1; M+H=332, $t_R$=2.1 min) indicated 100% pure product.

Intermediate A-1:

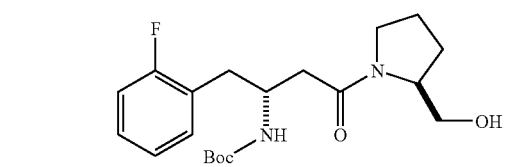

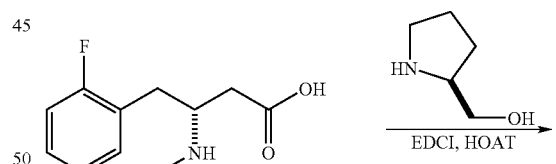

To a mixture of (3R)-3-(Boc-amino)-4-(2-fluorophenyl)butanoic acid (59.1 mg, 0.20 mmol), HOAT (40.8 mg, 0.30 mmol) and EDCI (115 mg, 0.60 mmol) in methylene chloride (1 mL) was added (S)-(+)-2-pyrrolidine methanol. The reaction was stirred at room temperature for 3 hours and concentrated. The residue was partitioned between saturated aqueous sodium bicarbonate and ethyl acetate. The layers were separated and the aqueous layer was extracted with ethyl acetate (2×). The combined organic layers were washed once with saturated aqueous sodium bicarbonate, twice with saturated aqueous ammonium chloride, once with brine, dried with sodium sulfate and concentrated in vacuo to give Intermediate A-1 as a glassy material (74.6 mg, 98% yield): LCMS Method 1: M+H=381; LC Method 1: $t_R$=3.1 mm.

Boc Removal Process 1:

To a solution of an N-Boc protected amine (0.06 mmol) in methylene chloride (0.6 mL) was added TFA (0.3 mL). The resulting mixture was stirred at room temperature for 1 hour and then concentrated in vacuo. The residue was purified using Cartridge Method 1. The collected fractions containing pure product are combined, concentrated in vacuo, and lyophilized to afford product amine as the trifluoroacetic acid salt.

Intermediate A-2:

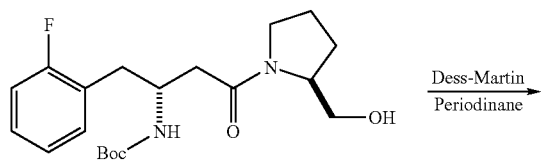

-continued

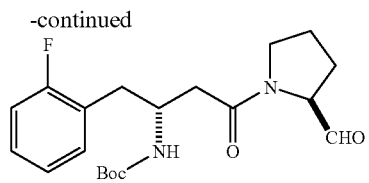

To a solution of Intermediate A-1 (2.8 g, 7.4 mmol) in methylene chloride (70 mL) was added Dess-Martin Periodinane (4.7 g, 11.1 mmol). The reaction was stirred at room temperature for 45 minutes and partially concentrated. The residue was diluted with ethyl ether and then washed twice with a 1:1 solution of 10% of $Na_2S_2O_3$ aqueous solution and saturated aqueous sodium bicarbonate. The combined aqueous solutions were back-extracted with ethyl ether. The combined organic layers were washed with brine, dried with sodium sulfate and evaporated. Flash chromatography of the residue over silica gel (120 g), using 30%, 50% and 70% of ethyl acetate in heptane, gave Intermediate A-2 as a sticky semi-solid material (2.3 g, 82% yield): LCMS Method 1; M+H=379; LC Method 2: $t_R$=3.2 min.

Reductive Amination Procedure 1:

To a mixture of Intermediate A-2 (0.07 mmol) and an amine (0.07 mmol) in 1,2-dichloroethane (0.5 mL) was added sodium triacetoxyborohydride (21 mg, 0.10 mmol). The mixture was stirred for 40 minutes, quenched with saturated aqueous sodium bicarbonate (1 mL), extracted with ether (3×1 mL), the combined organic layers back washed with brine (1 mL), dried with sodium sulfate, and then solvent removed in vacuo. The residue was purified using Prep LC Method 1

Using Reductive Amination Procedure 1 and the Boc-Removal Process 1, the following compound was prepared:

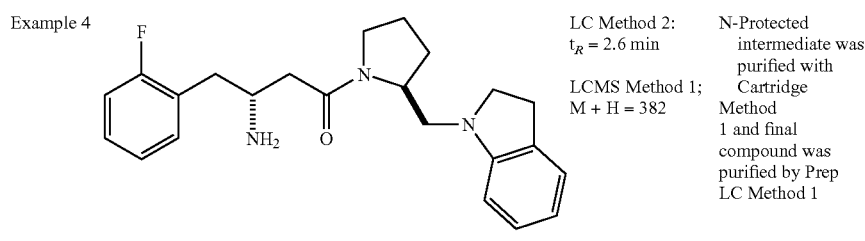

| Example 4 | LC Method 2: $t_R$ = 2.6 min | N-Protected intermediate was purified with Cartridge Method 1 and final compound was purified by Prep LC Method 1 |
| --- | --- | --- |
| | LCMS Method 1; M + H = 382 | |

Reductive Amination Procedure 2:

To a mixture of Intermediate A-2 (0.095 mmol) and an amine (0.142 mmol) in methanol (0.3 mL) was added zinc chloride (0.38 mL, 0.19 mmol, 0.5 M in THF). The resulting mixture was stirred at room temperature for 2.5 hours followed by addition of borane-pyridine complex (10.7 μL, 0.086 mmol, 8M). The reaction mixture was stirred at room temperature for 65 hours and quenched with water. The residue is purified using Prep LC Method 2 to provide the amine product.

Using the Reductive Amination Procedure 2 and the Boc-Removal Process 1, the following compounds were prepared and the final products purified using Prep LC Method 1:

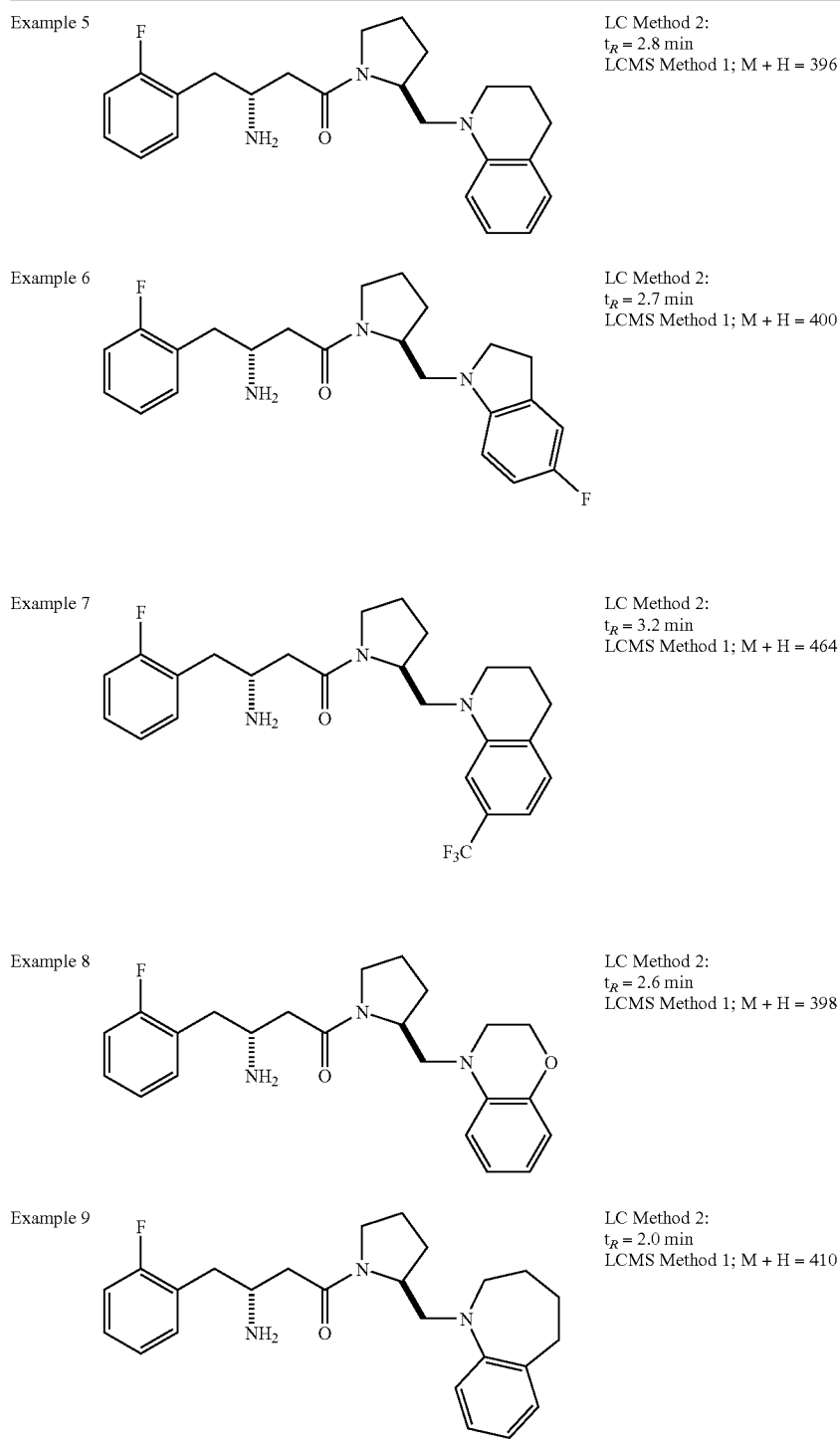

Intermediate B-1:

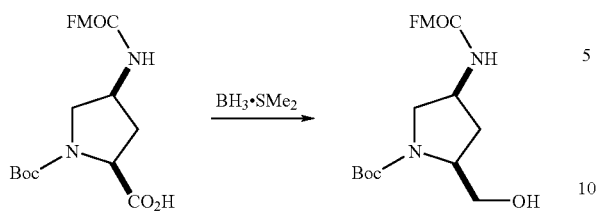

To a solution of N-Boc-cis-4-N-FMOC-amino-L-proline (2.03 g, 4.42 mmol) in THF (30 mL) was added 2 M borane-methyl sulfide complex in THF (8.84 mmol, 4.42 mL) dropwise at room temperature. The resulting mixture was heated to reflux for 1 hour and concentrated. The residue was partitioned between 20 mL of water and 60 mL of methylene chloride. The aqueous layer was back-extracted with methylene chloride (2x). The combined organic layers were washed with saturated aqueous sodium bicarbonate solution, brine, dried with sodium sulfate, and concentrated. Flash chromatography of the residue over silica (45 g), using 20%, 30%, and 50% of ethyl acetate in hexane gave Intermediate B-1 as an off-white powder (593 mg, 31%). The product was analyzed by LC (LC Method 1: $t_R$=3.8 min) and LCMS (LCMS Method 1: M+H=439).

Intermediate B-2:

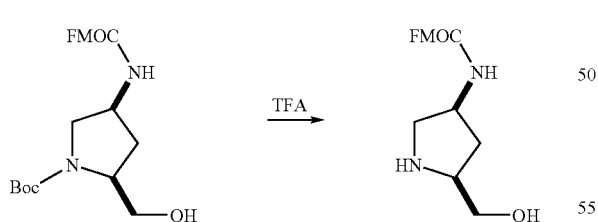

To a solution of Intermediate B-1 (582 mg, 1.33 mmol) in methylene chloride (6.0 mL) was added TFA (6.0 mL). The resulting mixture was stirred at room temperature for 1.5 hours and concentrated. The residue was then dissolved in chloroform, washed with saturated sodium bicarbonate solution and the aqueous layer was back extracted twice with chloroform. The combined organic layers were washed with brine, dried with sodium sulfate and concentrated to give the crude Intermediate B-2 as a pale yellow solid (500 mg, quantitative yield) which was used for next step without further purification.

Intermediate B-3 was produced as follows:

1) (3R)-3-(Boc-amino)-4-(2-fluorophenyl)butanoic acid was coupled with Intermediate B-2 as described in the procedure for Intermediate A-1
2) Oxidation to the aldehyde was accomplished using the procedure described for Intermediate A-2.
3) Reductive amination with 2-fluoroaniline was carried using Reductive Amination Procedure 2.

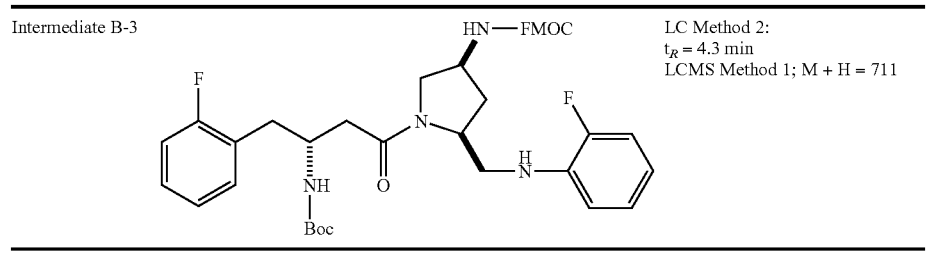

Intermediate B-3

LC Method 2:
$t_R$ = 4.3 min
LCMS Method 1; M + H = 711

Example 10

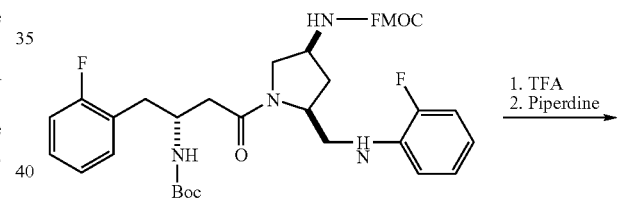

1. TFA
2. Piperdine

Using the Boc-Removal Process 1, the Boc group of Intermediate B-3 was removed using TFA. The deprotected compound (20 mg, 0.024 mmol) in DMF (0.95 mL) was treated with piperidine (0.5 mL). After stirring at room temperature for 30 minutes the mixture was concentrated, purified using Prep LC Method 1, and lyophilized to provide Example 70 as a light grey solid (13 mg, 75% yield). The product was analyzed by LC (LC Method 3: $t_R$=1.3 min) and LCMS (LCMS Method 1: M+H=389).

Intermediate E-4:

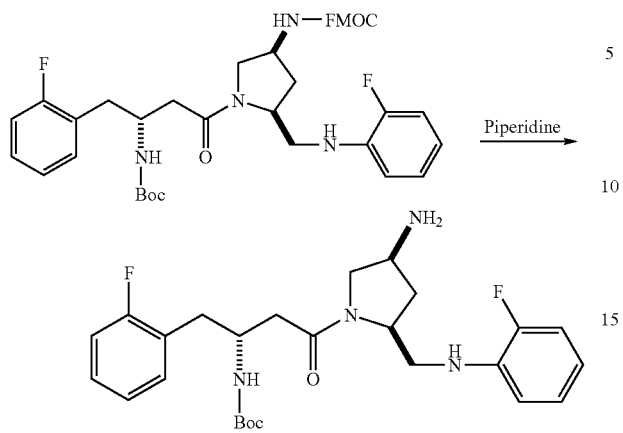

To a solution of Intermediate B-3 (165 mg, 0.23 mmol) in DMF (1.9 mL) was added piperidine (0.1 mL). The resulting mixture was stirred at room temperature for 20 minutes and evaporated. The residue was purified with silica (12 g), eluted with 5% methanol (containing about 0.1% of ammonia) in methylene chloride. The collected fractions were concentrated in vacuo to provide Intermediate B-4 as an off-white solid (88 mg, 77% yield). The product was analyzed by LC (LC Method 3: $t_R$=2.8 min) and LCMS (LCMS Method 1: M+H=489).

Using acetic acid and the method of acylation described for the preparation of Intermediate A-1 followed by the Boc-Removal Process 1, Example 11 was produced:

To a solution of Intermediate B-4 (21 mg, 0.043 mmol) in acetonitrile (0.4 mL) was added trimethylsilyl isocyanate at room temperature. The resulting mixture was stirred at room temperature for 3 hours and evaporated. The residue was dissolved in methylene chloride (0.4 mL), followed by the addition of TFA (0.25 mL). After stirring for 1 hour, the mixture was purged with nitrogen to remove the organic solvent. The residue was then purified using Prep LC Method 1 and lyophilized to provide Example 12 as an off-white powder (23 mg, 82% yield). The product was analyzed by LC (LC Method 3: $t_R$=2.0 min) and LCMS (LCMS Method 1: M+H=432).

Example 11

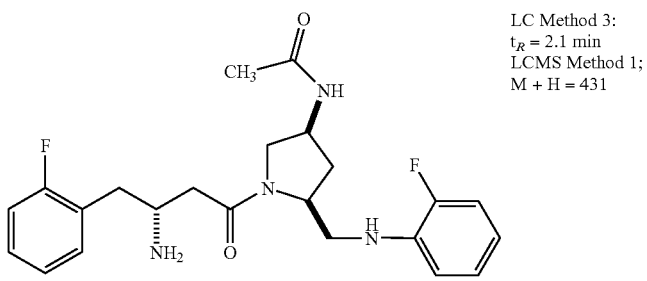

LC Method 3:
$t_R$ = 2.1 min
LCMS Method 1;
M + H = 431

Example 12

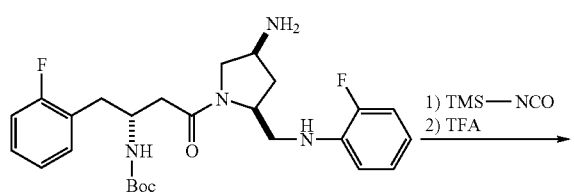

1) TMS—NCO
2) TFA

Using the procedure described for the preparation of Intermediate B-1 the following compound was prepared from N-Boc-trans-4-N-FMOC-amino-L-proline:

| Intermediate C-1 | | |
|---|---|---|
| | 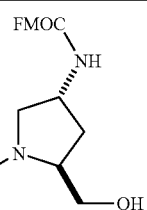 | LC Method 2:<br>$t_R$ = 3.7 min<br>LCMS Method 1;<br>M + H = 439 |

Intermediate C-2:

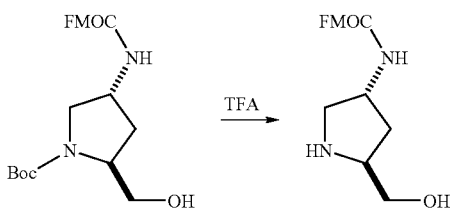

To a solution of Intermediate C-1 (27 mg, 0.06 mmol) in methylene chloride (0.5 mL) was added TFA (0.5 mL). The resulting mixture was stirred at room temperature for 1 hour and concentrated to give TFA salt of Intermediate C-2 as a sticky oil (28 mg, quantitative yield). The product was analyzed by LC (LC Method 3: $t_R$=2.3 min) and LCMS (LCMS Method 1: M+H=339).

ride, once with brine, dried with sodium sulfate and concentrated. The crude residue was purified using silica gel chromatography (45 g) eluting with 50% to 80% of ethyl acetate in hexane to give Intermediate C-3 as a white solid (327 mg, 46% yield). The product was analyzed by LC (LC Method 3: $t_R$=4.0 min) and LCMS (LCMS Method 1: M+H=618).

Example 13

Example 13 was produced from Intermediate C-3 as follows:
1) Oxidation of the alcohol in Intermediate C-3 to the aldehyde was accomplished using the procedure described for Intermediate A-2.
2) Reductive amination with 2-fluoroaniline was carried out using Reductive Amination Procedure 2.
3) FMOC removal was accomplished as described for Intermediate B-4.
4) Boc removal was accomplished using Boc-Removal Process 1.

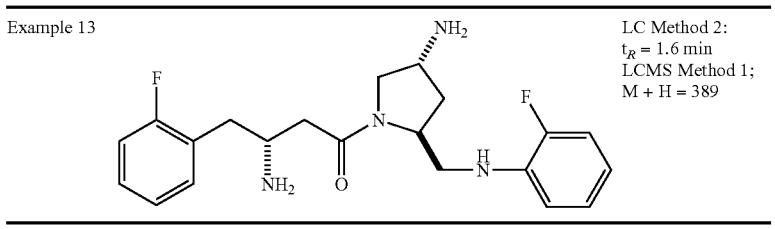

Example 13

LC Method 2:
$t_R$ = 1.6 min
LCMS Method 1;
M + H = 389

Intermediate C-3:

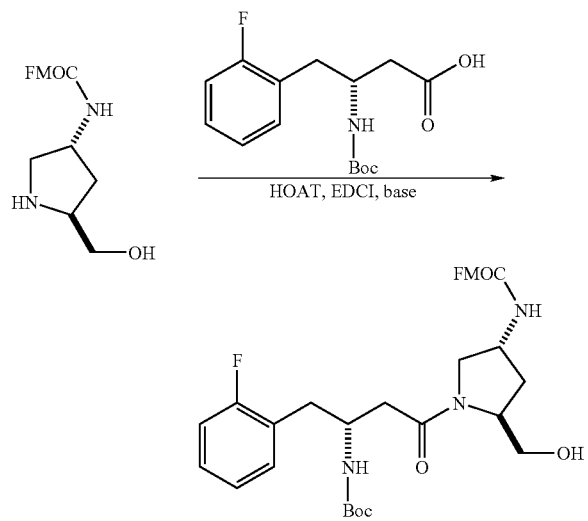

To a solution of Intermediate C-2 (710 mg, 1.57 mmol) in methylene chloride (15 mL) was added 4-methylmorpholine (0.52 μL, 4.71 mmol), HOAT (213 mg, 1.57 mmol), Boc-(R)-3-amino-4-(fluoro-phenyl)-butyric acid (467 mg, 1.57 mmol) and EDCI (600 mg, 3.13 mmol). The reaction mixture was stirred at room temperature for 3 hours and concentrated. The residue was partitioned between saturated aqueous sodium bicarbonate solution and ethyl acetate. The aqueous layer was extracted twice with ethyl acetate. The combined organic layers were washed once with saturated aqueous sodium bicarbonate, twice with saturated aqueous ammonium chlo- Intermediate D-1:

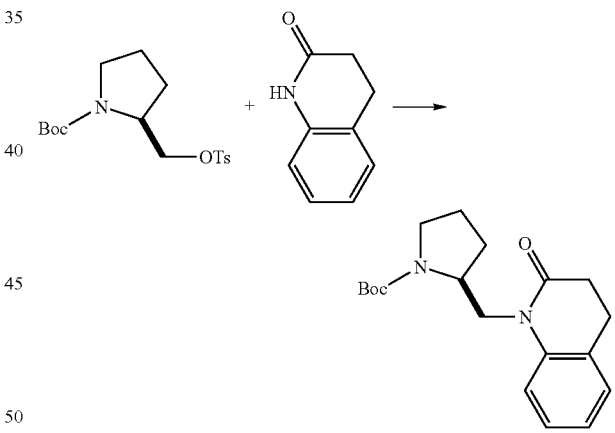

To the benzolactam (221 mg, 1.5 mmol) in DMF (3 mL) at 0° C. was added 60% NaH in an oil dispersion (80 mg, 2.0 mmol). The mixture was brought to room temperature at which point the tosylate was added. The mixture was then heated at 100° C. for 160 minutes. Ethyl acetate (5 mL) was added and the solution washed with water (3×5 mL) followed by drying with magnesium sulfate. Filtration, concentration, and purification by silica gel chromatography eluting with 0.7% methanol in methylene chloride gave the crude product. This was further purified by passing the material through a small column of C18-bound silica gel (J. T. Baker #7025-01) and eluting the product with 70% methanol in water. This provided 80 mg (0.24 mmol) of Intermediate D-1 as a glassy white oil. The product was analyzed by LC (LC Method 3: $t_R$=3.5 min) and LCMS (LCMS Method 1: M+H+Na=353).

Intermediate D-2:

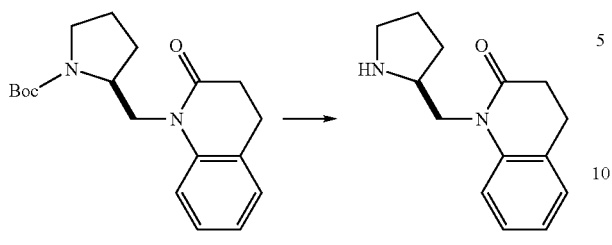

To the Intermediate D-1 (80 mg, 0.24 mmol) in methylene chloride (1 mL) was added TFA (1 mL). At approximately 1.5 hours the volatiles were removed in vacuo, the residue dissolved in methylene chloride (3 mL), washed with saturated aqueous sodium bicarbonate, dried with magnesium sulfate, and concentrated to provide Intermediate D-2 (27 mg, 0.12 mmol) as a pale yellow oil. The product was analyzed by LC (LC Method 3: $t_R$=3.5 min) and LCMS (LCMS Method 1: M+H=231).

Intermediate D-3:

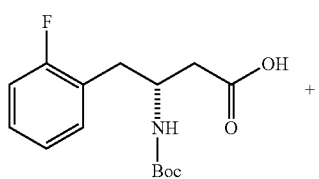

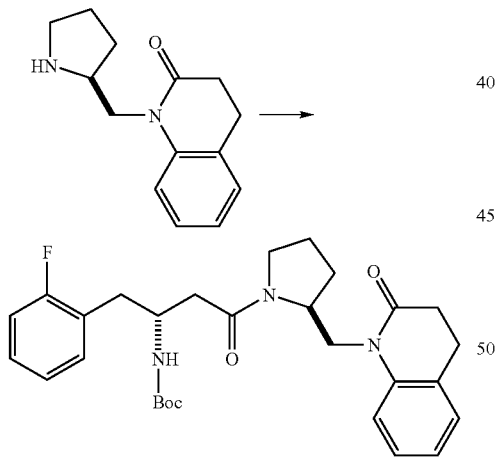

To (3R)-3-(Boc-amino)-4-(2-fluorophenyl)butanoic acid (36 mg, 0.12 mmol) in acetonitrile (0.4 mL) were added HOAT (25 mg, 0.18 mmol) and EDCI (46 mg, 0.24 mmol), the solution aged 5 minutes followed by addition of the Intermediate D-2 (27 mg, 0.12 mmol). After approximately 40 minutes ethyl acetate (2 mL) was added and the mixture washed successively with 2×2 mL of saturated aqueous sodium bicarbonate, 2×2 mL of saturated aqueous ammonium chloride, and then 2 mL of water. The ethyl acetate layer was dried with magnesium sulfate, filtered, and concentrated to provide Intermediate D-3 (43 mg, 0.84 mmol) as an off-white oily solid. The product was analyzed by LC (LC Method 3: $t_R$=3.7 min) and LCMS (LCMS Method 1: M+H=510).

Example 14

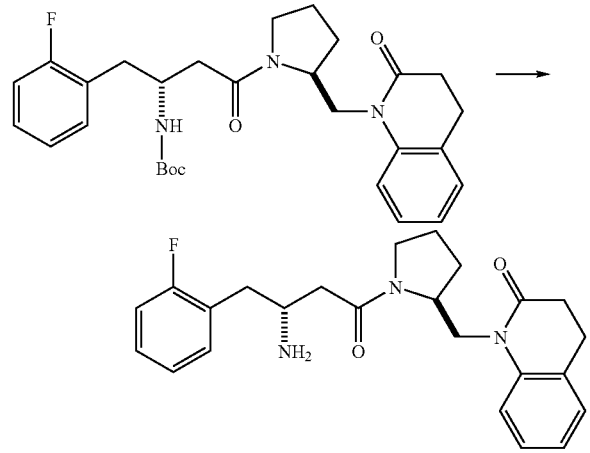

To Intermediate D-3 (43 mg, 0.084 mmol) in methylene chloride (1 mL) was added TFA (1 mL). At approximately 45 minutes the volatiles were removed in vacuo and the residue purified using a 2.5 g UCT C-18 cartridge (#CEC181(2500)6) eluting product with 20-30% methanol in water to yield Example 14 (15 mg, 0.029) as a pale yellow foam. The product was analyzed by LC (LC Method 3: $t_R$=2.2 min) and LCMS (LCMS Method 1: M+H=410).

We claim:

1. A compound of the formula

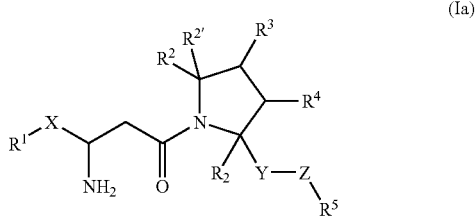

(Ia)

wherein:
$R^1$ is selected from aryl, heteroaryl or cycloheteroalkyl, wherein said aryl or heteroaryl may optionally be substituted with 1-5 substituents selected from the group consisting of halo, $C_{1-6}$ alkyl, and $C_{1-6}$ polyhaloalkyl, and said cycloheteroalkyl may optionally be substituted with 1-5 substituents selected from the group consisting of $C_{1-6}$ alkyl, halo, oxo (=O) and $C_{1-6}$ perhaloalkyl;

$R^2$ and $R^{2'}$ are each independently selected from hydrogen, $C_{1-6}$ alkyl, and $C_{1-6}$ perhaloalkyl;

$R^3$ and $R^4$ are each independently selected from hydrogen, $OR^6$ and $NR^7R^8$, wherein at least one of $R^3$ and $R^4$ is not hydrogen;

$R^5$ is selected from aryl and heteroaryl wherein said aryl and heteroaryl may optionally be substituted with 1-5 substituents selected from the group consisting of halo, $C_{1-6}$ alkyl, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkoxycarbonyl, $C_{2-6}$ alkenyl, $C_{2-6}$ alkynyl, $C_{3-6}$ cycloalkyl, C$_{3-6}$ cycloalkylalkyl, polycycloalkyl, heteroarylamino, arylamino, cycloheteroalkyl, cycloheteroalkylakyl, hydroxy, C$_{1-6}$ hydroxyalkyl, nitro, cyano, amino, C$_{1-6}$ alkylamino, C$_{1-6}$ dialkylamino, thiol, C$_{1-6}$ alkylthio, aminocarbonyl, C$_{2-6}$ alkynylaminocarbonyl, C$_{1-6}$ alkylaminocarbonyl, C$_{2-6}$ alkenylaminocarbonyl, C$_{1-6}$ alkylcarbonyloxy, C$_{1-6}$ alkylcarbonylamino, arylcarbonylamino, heteroarylcarbonylamino, C$_{1-6}$ alkylsulfonylamino, arylsulfonylamino, heteroarylsulfonylamino, arylsulfonyl, heteroarylsulfonyl, and sulfonamido;

R$^6$ is selected from hydrogen, C$_{1-6}$ alkyl, and C$_{3-6}$ cycloalkyl;

R$^7$ and R$^8$ are each independently selected from hydrogen, C$_{1-6}$ alkyl, C$_{3-6}$ cycloalkyl, —CO—(C$_{1-6}$ alkyl), —CO-aryl, —CO-heteroaryl, —CONH$_2$, —CONH(C$_{1-6}$ alkyl), CON(C$_{1-6}$ alkyl)$_2$, —SO$_2$(C$_{1-6}$ alkyl), —SO$_2$-aryl, and —SO$_2$-heteroaryl;

X is a methylene group or a bond, wherein the methylene group may be optionally substituted with one or two fluorine atoms;

Y is a methylene group, wherein said methylene group may be optionally substituted with one or two fluorine atoms, or Y and Z together may optionally form a bond;

Z is selected from a bond, —NR$^6$—, —O—, —SO$_n$—, —N(R$^6$)SO$_2$— and —SO$_2$N(R$^6$)—, or Z and R$^5$ may be taken together to form

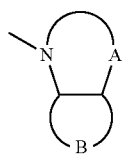

wherein A forms a 5 to 8 membered cycloheteroalkyl and B is a fused 5 to 7 member ring system selected from aryl and heteroaryl, wherein said ring system may be optionally substituted with one to five groups selected from the group consisting of halo, C$_{1-6}$ alkyl, C$_{1-6}$ polyhaloalkyl, C$_{1-6}$ alkoxy, C$_{1-6}$ haloalkoxy, C$_{1-6}$ polyhaloalkoxy, C$_{1-6}$ alkoxycarbonyl, C$_{2-6}$ alkenyl, C$_{2-6}$ alkynyl, C$_{3-6}$ cycloalkyl, C$_{3-6}$ cycloalkylalkyl, polycycloalkyl, heteroarylamino, arylamino, cycloheteroalkyl, cycloheteroalkylalkyl, hydroxy, C$_{1-6}$ hydroxyalkyl, nitro, cyano, amino, C$_{1-6}$ alkylamino, C$_{1-6}$ dialkylamino, thiol, C$_{1-6}$ alkylthio, aminocarbonyl, C$_{2-6}$ alkynylaminocarbonyl, C$_{1-6}$ alkylaminocarbonyl, C$_{2-6}$ alkenylamino-carbonyl, C$_{1-6}$ alkylcarbonyloxy, C$_{1-6}$ alkylcarbonylamino, arylcarbonylamino; heteroarylcarbonylamino, C$_{1-6}$ alkylsulfonylamino, arylsulfonylamino, heteroarylsulfonylamino, C$_{1-6}$ alkylaminocarbonylamino, C$_{1-6}$ alkoxycarbonylamino, C$_{1-6}$ alkylsulfonyl, arylsulfonyl, heteroarylsulfonyl, and sulfonamido; and n is 0-2.

2. A compound of the formula

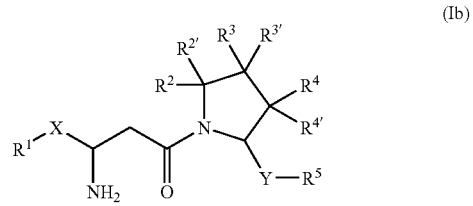

(Ib)

wherein

R$^1$ is selected from aryl, heteroaryl or cycloheteroalkyl, wherein said aryl or heteroaryl may optionally be substituted with 1-5 substituents selected from the group consisting of halo, C$_{1-6}$alkyl, and C$_{1-6}$ polyhaloalkyl, and said cycloheteroalkyl may optionally be substituted with 1-5 substituents selected from the group consisting of C$_{1-6}$ alkyl, halo, oxo (═O) and C$_{1-6}$ perhaloalkyl;

R$^2$ and R$^{2'}$ are each independently selected from hydrogen, C$_{1-6}$ alkyl, and C$_{1-6}$ perhaloalkyl;

R$^3$, R$^{3'}$, R$^4$, R$^{4'}$ are each independently selected from hydrogen, fluorine, C$_{1-6}$ alkyl, C$_{1-6}$ perhaloalkyl, OR$^6$, and NR$^7$R$^8$;

R$^5$ is selected from aryl and heteroaryl, wherein said aryl and heteroaryl may optionally be substituted with 1-5 substituents selected from the group consisting of halo, C$_{1-6}$ alkyl, C$_{1-6}$ haloalkyl, C$_{1-6}$ polyhaloalkyl, C$_{1-6}$ alkoxy, C$_{1-6}$ haloalkoxy, C$_{1-6}$ polyhaloalkoxy, C$_{1-6}$ alkoxycarbonyl, C$_{2-6}$ alkenyl, C$_{2-6}$ alkynyl, C$_{3-6}$ cycloalkyl, C$_{3-6}$ cycloalkylalkyl, polycycloalkyl, heteroarylamino, arylamino, cycloheteroalkyl, cycloheteroalkylalkyl, hydroxy, C$_{1-6}$ hydroxyalkyl, nitro, cyano, amino, C$_{1-6}$ alkylamino, C$_{1-6}$ dialkylamino, thiol, C$_{1-6}$ alkylthio, aminocarbonyl, C$_{1-6}$ alkynylaminocarbonyl, C$_{1-6}$ alkylaminocarbonyl, C$_{2-6}$ alkenylaminocarbonyl, C$_{1-6}$ alkylcarbonyloxy, C$_{1-6}$ alkylcarbonylamino, arylcarbonylamino, heteroarylcarbonylamino, C$_{1-6}$ alkylsulfonylamino, arylsulfonylamino, heteroarylsulfonylamino, C$_{1-6}$ alkylaminocarbonylamino, C$_{1-6}$ alkoxycarbonylamino, C$_{1-6}$ alkylsulfonyl, arylsulfonyl, heteroarylsulfonyl and sulfonamido, or R$^5$ is

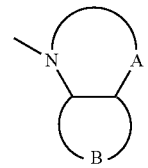

wherein A forms a 5 to 8 membered substituted or unsubstituted cycloheteroalkyl and B is a fused 5 to 7 member ring system selected from aryl and heteroaryl, wherein said ring system may be optionally substituted with one to five groups selected from the group consisting of halo, C$_{1-6}$ alkyl, C$_{1-6}$ polyhaloalkyl, C$_{1-6}$ alkoxy, C$_{1-6}$ haloalkoxy, C$_{1-6}$ polyhaloalkoxy, C$_{1-6}$ alkoxycarbonyl, C$_{1-6}$ alkenyl, C$_{1-6}$ alkynyl, C$_{3-6}$ cycloalkyl, C$_{3-6}$ cycloalkylalkyl, polycycloalkyl, heteroarylamino, arylamino, cycloheteroalkyl, cycloheteroalkylalkyl, hydroxy, C$_{1-6}$ hydroxyalkyl, nitro, cyano, amino, C$_{1-6}$ alkylamino, C$_{1-6}$ dialkylamino, thiol, C$_{1-6}$ alkylthio, aminocarbonyl, C$_{1-6}$ alkynylaminocarbonyl, C$_{1-6}$ alkylaminocarbonyl, C$_{1-6}$ alkenylaminocarbonyl, C$_{1-6}$ alkylcarbonyloxy, C$_{1-6}$ alkylcarbonylamino, arylcarbonylamino, heteroarylcarbonylamino, $C_{1-6}$ alkylsulfonylamino, arylsulfonylamino, heteroarylsulfonylamino, $C_{1-6}$ alkylaminocarbonylamino, $C_{1-6}$ alkoxycarbonylamino, $C_{1-6}$ alkylsulfonyl, arylsulfonyl, heteroarylsulfonyl and sulfonamido;

$R^6$ is selected from hydrogen, $C_{1-6}$ alkyl and $C_{3-6}$ cycloalkyl;

$R^7$ and $R^8$ are each independently selected from hydrogen, $C_{1-6}$ alkyl, $C_{3-6}$ cycloalkyl, —CO—($C_{1-6}$ alkyl), —CO-aryl, —CO-heteroaryl, —CONH$_2$, —CONH($C_{1-6}$ alkyl), CON($C_{1-6}$ alkyl)$_2$,—SO$_2$($C_{1-6}$ alkyl), —SO$_2$-aryl and —SO$_2$-heteroaryl;

X is a methylene group or a bond, wherein the methylene group may be optionally substituted with one or two fluorine atoms;

Y is a methylene group, wherein said methylene group may be optionally substituted with one or two fluorine atoms, or a bond; and n is 0-2.

3. The compound of claim 1 having the structure

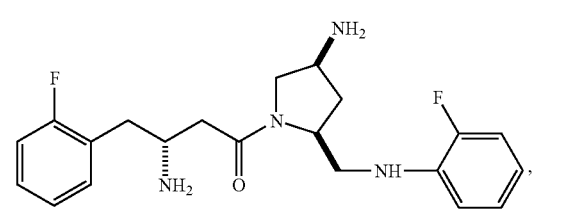

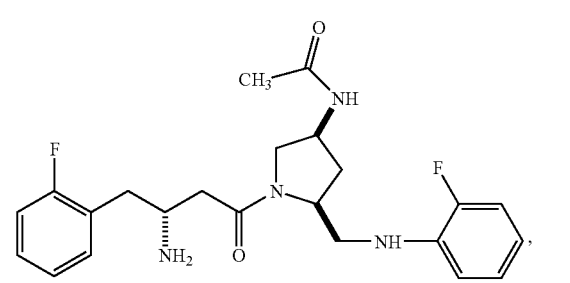

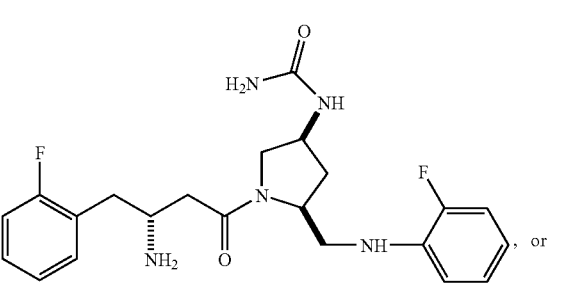

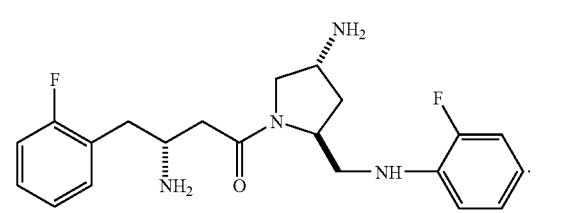

4. The compound of claim 2 having the structure

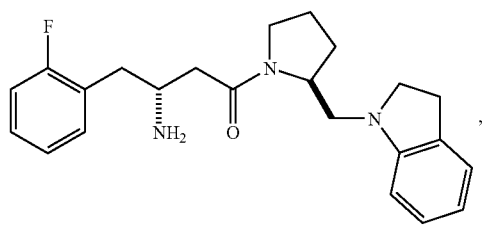

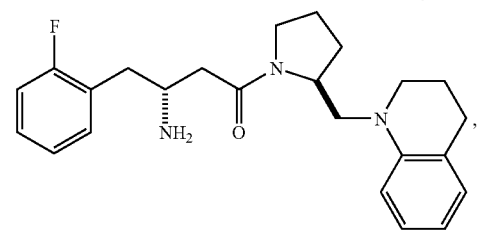

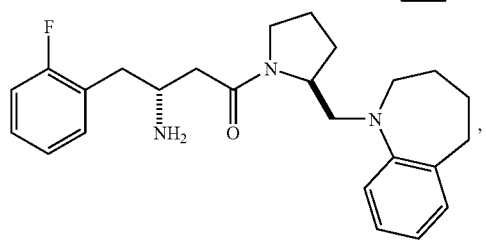

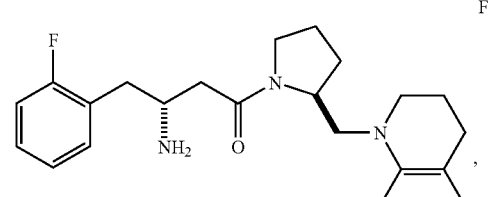

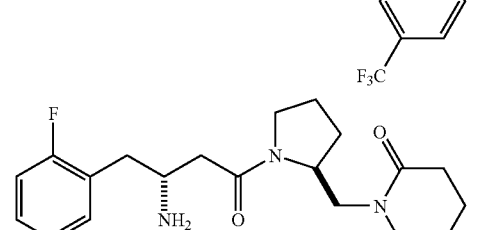

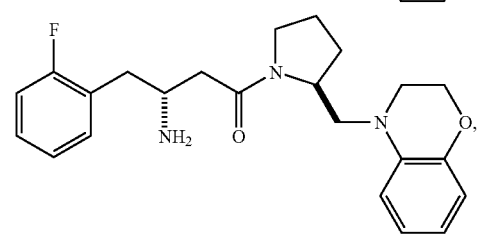

-continued

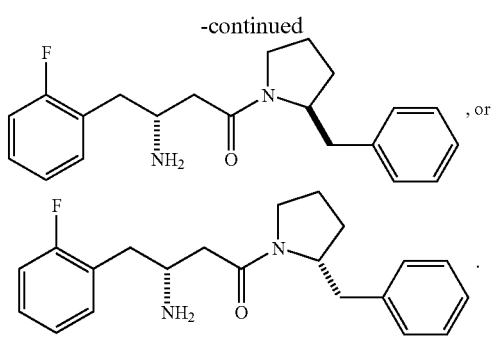

5. A pharmaceutical combination comprising a compound of formula Ia as defined in claim 1, and at least one therapeutic agent selected from the group consisting of an antidiabetic agent, an anti-obesity agent, an anti-hypertensive agent, an anti-atherosclerotic agent and a lipid-lowering agent.

6. The pharmaceutical combination as defined in claim 5 wherein the therapeutic agent is an antidiabetic agent.

7. The combination as defined in claim 6 wherein the antidiabetic agent is at least one agent selected from the group consisting of a biguanide, a sulfonyl urea, a glucosidase inhibitor, a PPAR gamma agonist, a PPAR alpha/gamma dual agonist, an aP2 inhibitor, a SGLT2 inhibitor, an insulin sensitizer, a glucagonlike peptide-1 (GLP-1), insulin and a meglitinide.

8. The combination as defined in claim 7 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, isaglitazone, repaglinide and nateglinide.

9. The combination as defined in claim 6 wherein the compound is present in a weight ratio to the antidiabetic agent in the range of about 0.01 to about 300:1.

10. The combination as defined in claim 5 wherein the anti-obesity agent is at least one agent selected from the group consisting of a beta 3 adrenergic agonist, a lipase inhibitor, a serotonin (and dopamine) reuptake inhibitor, a thyroid receptor beta compound and an anorectic agent.

11. The combination as defined in claim 10 wherein the anti-obesity agent is at least one agent selected from the group consisting of orlistat, sibutramine, topiramate, axokine, dexamphetamine, phentermine, phenyipropanolamine and mazindol.

12. The combination as defined in claim 5 wherein the lipid lowering agent is at least one agent selected from the group consisting of an MTP inhibitor, cholesterol ester transfer protein, an HMG CoA reductase inhibitor, a squalene synthetase inhibitor, a fibric acid derivative which is fenofibrate, gemfibrozil, clofibrate, benzafibrate, ciprofibrate, clinofibrate or probucol, an upregulator of LDL receptor activity, a lipoxygenase inhibitor, or an ACAT inhibitor.

13. The combination as defined in claim 12 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate and avasimibe.

14. The combination as defined in claim 5 wherein the compound as defined in claim 1 is present in a weight ratio to the lipid-lowering agent in the range of about 0.01 to about 100:1.

15. A method for treating diabetes, diabetic retinopathy, diabetic neuropathy, diabetic nephropathy, wound healing, insulin resistance, hyperglycemia, hyperinsulinemia, Syndrome X, elevated blood levels of free fatty acids or glycerol, hyperlipidemia, obesity, hypertriglyceridemia, atherosclerosis or hypertension, which comprises administering to a mammalian species in need of treatment a therapeutically effective amount of a compound of formula Ia as defined in claim 1.

16. The method according to claim 15 further comprising administering, concurrently or sequentially, a therapeutically effective amount of at least one additional therapeutic agent selected from the group consisting of an antidiabetic agent, an anti-obesity agent, an anti-hypertensive agent, an anti-atherosclerotic agent, an agent for inhibiting allograft rejection in transplantation and a lipid-lowering agent.

17. A pharmaceutical combination comprising a compound of formula Ib as defined in claim 2 and at least one therapeutic agent selected from the group consisting of an antidiabetic agent, an anti-obesity agent, an anti-hypertensive agent, an anti-atherosclerotic agent and a lipid-lowering agent.

18. A compound having the structure

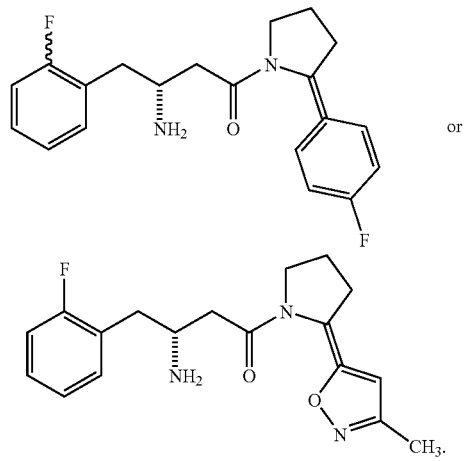

19. A method for treating diabetes, diabetic retinopathy, diabetic neuropathy, diabetic nephropathy, wound healing, insulin resistance, hyperglycemia, hyperinsulinemia, Syndrome X, elevated blood levels of free fatty acids or glycerol, hyperlipidemia, obesity, hypertriglyceridemia, atherosclerosis or hypertension, which comprises administering to a mammalian species in need of treatment a therapeutically effective amount of a compound of formula Ib as defined in claim 2.

20. The method according to claim 19 further comprising administering, concurrently or sequentially, a therapeutically effective amount of at least one additional therapeutic agent selected from the group consisting of an antidiabetic agent, an anti-obesity agent, an anti-hypertensive agent, an anti-atherosclerotic agent, an agent for inhibiting allograft rejection in transplantation and a lipid-lowering agent.

* * * * *